US011937862B2

(12) United States Patent
Sweitzer

(10) Patent No.: US 11,937,862 B2
(45) Date of Patent: Mar. 26, 2024

(54) STRIKING ASSEMBLY AND SURGICAL TOOL ASSEMBLY

(71) Applicant: Shukla Medical, St. Petersburg, FL (US)

(72) Inventor: Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 820 days.

(21) Appl. No.: 16/746,023

(22) Filed: Jan. 17, 2020

(65) Prior Publication Data

US 2020/0229857 A1 Jul. 23, 2020

Related U.S. Application Data

(60) Provisional application No. 62/794,030, filed on Jan. 18, 2019.

(51) Int. Cl.
*A61B 17/92* (2006.01)
*A61B 17/00* (2006.01)
*A61B 17/16* (2006.01)

(52) U.S. Cl.
CPC .... *A61B 17/92* (2013.01); *A61B 2017/00424* (2013.01); *A61B 17/1604* (2013.01)

(58) Field of Classification Search
CPC .............. A61B 17/92; A61B 2017/922; A61B 2090/0436; B25G 3/38; B25G 1/06; B25D 3/00; B25D 5/00; B26B 29/02
USPC .................................................... 30/167, 295
See application file for complete search history.

(56) References Cited

U.S. PATENT DOCUMENTS

| 108,141 | A | * | 10/1870 | Houseman et al. | .... B26B 29/02 30/340 |
| 268,997 | A | * | 12/1882 | Brion | ..................... A22B 5/168 30/286 |
| 634,287 | A | * | 10/1899 | Deptner | .................. B26B 29/02 30/286 |
| 718,150 | A | * | 1/1903 | Perry | ...................... F41C 27/18 30/296.1 |
| 1,128,871 | A | * | 2/1915 | Holik | ....................... B25G 3/02 403/243 |

(Continued)

FOREIGN PATENT DOCUMENTS

| JP | 2005246036 A | 9/2005 |
| JP | 2013511351 A | 4/2013 |
| WO | 2018045105 A1 | 3/2018 |

OTHER PUBLICATIONS

Written Opinion of International Searching Authority dated Nov. 27, 2017 in International Application No. PCT/US2017/49492.

(Continued)

*Primary Examiner* — David W Bates
(74) *Attorney, Agent, or Firm* — Kim IP Law Group LLC

(57) ABSTRACT

A surgical tool assembly having a striking assembly is disclosed. The surgical tool assembly includes a handle for attachment to a tool, and a striking assembly for attachment to the handle. The striking assembly includes a frame, an impact plate extending from the frame, and a guard attached to the frame and movable between a first position adjacent the frame and a second position. The second position may be distal to the frame, e.g., adjacent the handle.

18 Claims, 20 Drawing Sheets

(56) References Cited

U.S. PATENT DOCUMENTS

| | | | | |
|---|---|---|---|---|
| 1,299,084 A * | 4/1919 | Wilson | ............... | A22C 21/06 |
| | | | | 452/120 |
| 1,370,933 A * | 3/1921 | Isak | ............... | B25D 3/00 |
| | | | | 125/36 |
| 1,496,888 A * | 6/1924 | Kalinowski | ............... | F25C 5/043 |
| | | | | 30/295 |
| 1,755,351 A * | 4/1930 | Felardo | ............... | B26B 29/02 |
| | | | | 30/295 |
| 2,387,032 A * | 10/1945 | Lowry | ............... | B26B 3/00 |
| | | | | 30/286 |
| 2,702,488 A * | 2/1955 | January | ............... | B25F 1/02 |
| | | | | 125/36 |
| 2,889,726 A * | 6/1959 | Strabeck | ............... | B25D 3/00 |
| | | | | 81/487 |
| 2,901,824 A * | 9/1959 | Zullo | ............... | B26B 29/02 |
| | | | | 30/295 |
| 3,008,361 A * | 11/1961 | Henning | ............... | B25C 1/02 |
| | | | | 173/210 |
| D193,556 S | 9/1962 | Lebourg et al. | | |
| 3,121,938 A * | 2/1964 | Lind | ............... | B25G 1/00 |
| | | | | 407/29.15 |
| 3,538,605 A * | 11/1970 | Smith | ............... | B26B 29/02 |
| | | | | 30/295 |
| 4,133,362 A * | 1/1979 | Kolloch | ............... | B25D 3/00 |
| | | | | 30/295 |
| 4,150,675 A | 4/1979 | Comparetto | | |
| 4,403,725 A * | 9/1983 | Lawrence | ............... | B25C 1/02 |
| | | | | 227/147 |
| 4,716,894 A * | 1/1988 | Lazzeri | ............... | A61F 2/4609 |
| | | | | 606/91 |
| 4,987,682 A * | 1/1991 | Minnick | ............... | B26B 29/025 |
| | | | | 30/295 |
| D337,160 S | 7/1993 | Evans | | |
| 5,261,922 A | 11/1993 | Hood | | |
| 5,440,814 A * | 8/1995 | Hall | ............... | B26B 3/06 |
| | | | | 30/286 |
| 5,491,898 A * | 2/1996 | Riley | ............... | A62B 3/005 |
| | | | | 30/295 |
| 5,522,828 A * | 6/1996 | Malilay | ............... | B26B 29/025 |
| | | | | 30/329 |
| 5,581,893 A * | 12/1996 | Ouellette | ............... | B26B 29/025 |
| | | | | 30/286 |
| 5,632,090 A * | 5/1997 | Smith | ............... | B26B 3/08 |
| | | | | 15/236.1 |
| D385,164 S | 10/1997 | Hutchins et al. | | |
| 5,683,406 A | 11/1997 | Altobelli et al. | | |
| 5,730,231 A * | 3/1998 | Racodon | ............... | B25D 3/00 |
| | | | | 16/431 |
| 5,997,298 A | 12/1999 | Nowak | | |
| 6,076,431 A * | 6/2000 | Vasudeva | ............... | B25D 3/00 |
| | | | | 30/167 |
| D466,213 S | 11/2002 | Snitkin et al. | | |
| 6,493,892 B2 * | 12/2002 | Kang | ............... | B25C 3/006 |
| | | | | 7/125 |
| D503,800 S | 4/2005 | Ebner | | |
| 6,951,153 B2 * | 10/2005 | Berthlaume | ............... | B25C 9/00 |
| | | | | 81/437 |
| 6,986,504 B1 * | 1/2006 | Eby | ............... | B25C 11/00 |
| | | | | 81/20 |
| 7,159,747 B1 * | 1/2007 | Tanner | ............... | B25C 1/02 |
| | | | | 227/139 |
| D536,791 S | 2/2007 | Eskridge et al. | | |
| D554,256 S | 10/2007 | Eskridge et al. | | |
| D562,981 S | 2/2008 | Trissel et al. | | |
| 7,533,465 B1 * | 5/2009 | Frazer | ............... | B26B 29/02 |
| | | | | 30/151 |
| D598,724 S * | 8/2009 | Hsieh | ............... | D8/47 |
| D601,869 S | 10/2009 | Nelson | | |
| D603,231 S | 11/2009 | Fisher et al. | | |
| D610,399 S * | 2/2010 | Hamlin | ............... | D7/387 |
| 7,704,254 B2 | 4/2010 | Walen | | |
| D631,154 S | 1/2011 | Hamilton, Jr. | | |
| D699,342 S | 2/2014 | Suzuki | | |
| D699,348 S | 2/2014 | Morejon | | |
| 8,671,578 B1 * | 3/2014 | Frazer | ............... | B26B 1/08 |
| | | | | 30/162 |
| 8,740,912 B2 | 6/2014 | Stark | | |
| D742,002 S | 10/2015 | Fisher et al. | | |
| D745,349 S | 12/2015 | Hampton et al. | | |
| D745,350 S | 12/2015 | Hampton et al. | | |
| 9,358,694 B1 * | 6/2016 | Heumann | ............... | B26B 29/02 |
| D778,443 S | 2/2017 | Brannon | | |
| D802,763 S | 11/2017 | Sweitzer | | |
| 10,286,423 B1 * | 5/2019 | Armetta | ............... | A47L 13/34 |
| 11,084,086 B1 * | 8/2021 | Whaley | ............... | B25D 1/16 |
| 2001/0037114 A1 | 11/2001 | Dinger et al. | | |
| 2001/0039862 A1 * | 11/2001 | Eichhorn | ............... | B25G 1/01 |
| | | | | 82/160 |
| 2005/0097708 A1 * | 5/2005 | Crawford | ............... | B25G 1/01 |
| | | | | 16/431 |
| 2005/0228395 A1 * | 10/2005 | Auxepaules | ............... | A61F 2/4609 |
| | | | | 606/91 |
| 2006/0081585 A1 * | 4/2006 | Pierce | ............... | H05B 3/42 |
| | | | | 219/229 |
| 2006/0197070 A1 * | 9/2006 | Eby | ............... | B25D 1/045 |
| | | | | 254/25 |
| 2007/0101547 A1 * | 5/2007 | Egeland | ............... | B25G 1/102 |
| | | | | 16/430 |
| 2008/0221580 A1 * | 9/2008 | Miller | ............... | A61B 10/025 |
| | | | | 606/80 |
| 2009/0306669 A1 | 12/2009 | Takahashi | | |
| 2010/0100134 A1 | 4/2010 | Mocanu | | |
| 2010/0249785 A1 | 9/2010 | Betts | | |
| 2012/0024554 A1 * | 2/2012 | Boehm | ............... | B25H 7/045 |
| | | | | 173/162.2 |
| 2013/0180114 A1 * | 7/2013 | Brown | ............... | B25D 3/00 |
| | | | | 30/153 |
| 2013/0261630 A1 | 10/2013 | Courtney, Jr. et al. | | |
| 2014/0338196 A1 * | 11/2014 | Frazer | ............... | B25G 1/08 |
| | | | | 30/143 |
| 2016/0128716 A1 | 5/2016 | Cao et al. | | |
| 2016/0268068 A1 * | 9/2016 | Chiasson | ............... | H01H 9/24 |
| 2017/0000509 A1 | 1/2017 | Kato et al. | | |
| 2017/0043500 A1 * | 2/2017 | O'Brien | ............... | B28D 1/26 |
| 2017/0120021 A1 | 5/2017 | Krastev | | |
| 2019/0201008 A1 | 7/2019 | Sweitzer | ............... | A61B 17/1604 |

OTHER PUBLICATIONS

International Search Report dated Nov. 27, 2017 in International Application No. PCT/US2017/49492.

Japanese Office Action dated Nov. 12, 2019 in Japanese Patent Application No. 2019-512712.

* cited by examiner

STRIKING ASSEMBLY AND SURGICAL TOOL ASSEMBLY

CROSS-REFERENCE TO RELATED APPLICATIONS

This application claims the benefit of U.S. Provisional Patent Application No. 62/794,030, filed Jan. 18, 2019 and entitled "STRIKING ASSEMBLY FOR A SURGICAL TOOL," the entire disclosure of which is incorporated by reference herein for all purposes.

BACKGROUND OF THE INVENTION

Exemplary embodiments of the subject disclosure relate generally to the field of medical device implant extraction tools and, more specifically, to a surgical tool assembly having a striking assembly.

Handles allow for holding and manipulating surgical tools such as osteotomes. Oftentimes a surgeon must strike the handle with a tool such as a hammer or the like, for example to insert the surgical tool into the patient's bone or extract the surgical tool from the bone. Conventional striking assemblies are limited in their functionality in that they do not provide protection to a surgeon's hand when a striking tool is used adjacent to the hand and may inadvertently strike and injure the hand.

SUMMARY OF THE INVENTION

In accordance with an exemplary embodiment, the subject disclosure provides a surgical tool assembly having a striking assembly. The surgical tool assembly includes a handle for attachment to a tool, and a striking assembly for attachment to the handle. The striking assembly further includes a frame, an impact plate extending from the frame, and a guard attached to the frame and movable between a first position adjacent the frame and a second position adjacent the handle.

In an aspect of the subject disclosure, in the second position the guard is laterally adjacent the handle. In the second position, the guard is laterally adjacent a majority of a longitudinal length of the handle. The guard is attached to an anterior side of the frame. The handle attaches to a distal end of the striking assembly and a longitudinal axis of the handle is substantially aligned with a longitudinal axis of the frame of the striking assembly. The striking assembly further includes an attachment mechanism for attaching to the handle. The attachment mechanism includes a quick connect, and a pair of detents for operatively engaging cooperating detents on the handle.

The subject disclosure further provides a striking assembly for attachment to a surgical tool. The striking assembly includes a frame, an impact plate extending from the frame, and a guard attached to the frame and movable between a first position adjacent the frame and a second position distal to the frame.

In an aspect of the subject disclosure, the striking assembly further includes a lock mechanism for securing the guard in a fixed position relative to the frame. The striking assembly further includes an attachment mechanism for attaching to a surgical tool. The impact plate extends from about a proximal end of the frame and the guard is attached to about a distal end of the frame. The impact plate extends radially outwardly from the frame. The guard is attached to the same side of the frame that the impact plate extends from. The frame includes a positioning member having a first and a second positioning slot, and the guard is secured to the frame via the positioning member. The striking assembly further includes a lock that includes a keyed locking pin movable relative to the positioning member between an unlocking position and a locking position wherein in the locking position the keyed locking pin engages one of the first or second positioning slots. The lock further includes a biasing member biasing the keyed locking pin to the locking position. The frame further includes a stop to operatively engage the guard in the second position. The frame further includes a biasing actuator to operatively actuate the guard into the second position. The guard includes a base for attaching to the frame, and a curved guard body extending from the base. When in the second position, the curved guard body is distally spaced from a distal end of the frame. The guard further includes a curved distal end.

BRIEF DESCRIPTION OF THE SEVERAL VIEWS OF THE DRAWINGS

The following detailed description of an exemplary embodiment of the subject disclosure, will be better understood when read in conjunction with the appended drawings. For the purpose of illustrating the present disclosure, there are shown in the drawings an exemplary embodiment. It should be understood, however, that the subject application is not limited to the precise arrangements and instrumentalities shown.

DETAILED DESCRIPTION OF THE DRAWINGS

Figure 1A:
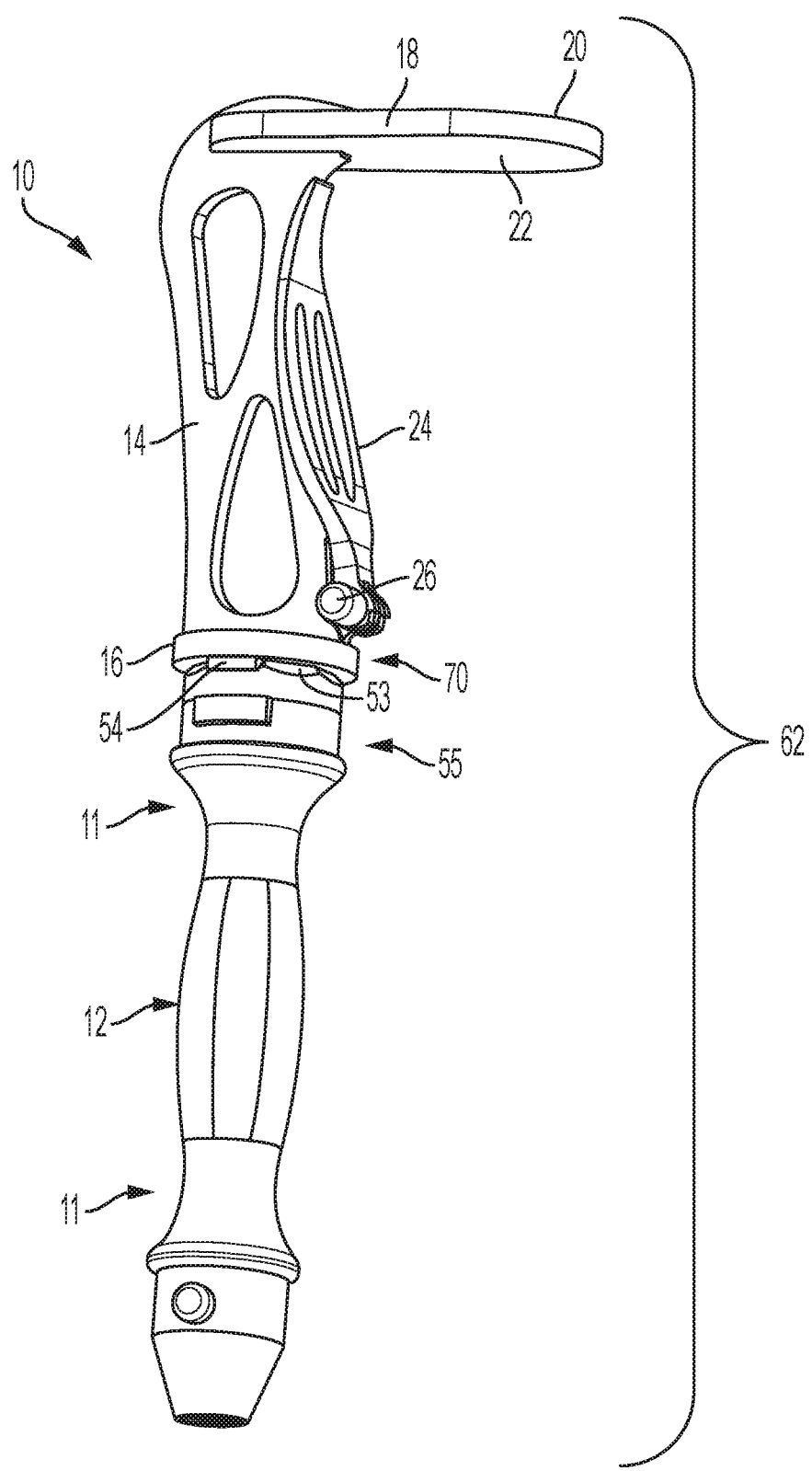
FIG. 1A is a perspective view of a surgical tool assembly in accordance with an exemplary embodiment of the subject disclosure shown with a guard in a retracted position.

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. The term "distal" means away from the center of a body. The term "proximal" means closer towards the center of a body and/or away from the "distal" end. The term "anterior" means in front of the center of a body. The term "posterior" means behind the center of a body and/or away from the "anterior" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

Certain terminology is used in the following description for convenience only and is not limiting. The words "right," "left," "upper," and "lower" designate directions in the drawings to which reference is made. The terminology includes the words above specifically mentioned, derivatives thereof, and words of similar import. With reference to a surgical tool assembly or a striking assembly, the "distal end" of the apparatus refers to the end of the apparatus towards the handle while the "proximal end" of the apparatus refers to the end of the apparatus towards the impact plate.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1B:
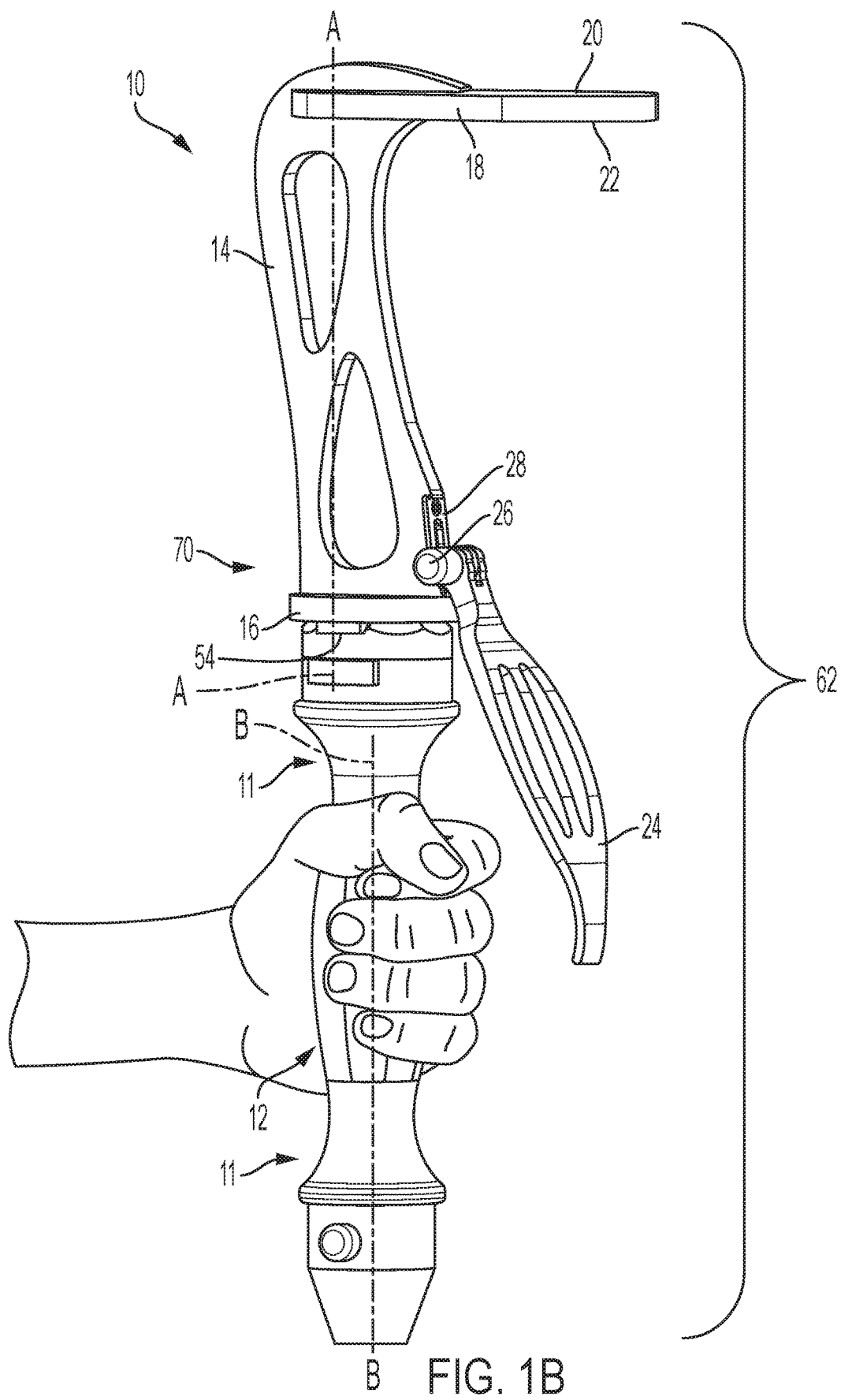
FIG. 1B is a perspective view of the surgical tool assembly of FIG. 1A shown with the guard in an extended position.

Referring to FIGS. 1A-11D there is shown an exemplary embodiment of a surgical tool assembly 62 in accordance with the subject disclosure. As shown in FIGS. 1A and 1B, the surgical tool assembly includes a handle 12 for attachment to a surgical tool (not shown) and a striking assembly 10 for attachment to the handle.

The handle 12 is generally an elongated member that is preferably rigid and sized sufficiently to be gripped by a hand of a user (FIG. 1B). As shown in FIGS. 1A-1B, the handle is generally a substantially cylindrical member having a longitudinal central axis and a substantially circular cross-section. However, the handle can have any cross-sectional shape such as hexagonal, polygonal, or any other cross-sectional shape suitable for its intended purpose or be contoured to more ergonomically conform to a user's hand. The handle can also be formed with a plurality of handle segments having different cross-sectional diameters.

Generally, the handle 12 is illustrated as straight, although it may have a lordotic curve or be otherwise bent or curved. The handle may have any desired length sufficient for its intended purpose.

The handle 12 includes gripping portions 11 that aid a user's ability to grip and move the surgical tool assembly 62. As shown in FIGS. 1A-1B, the gripping portion may be located adjacent a distal end of the handle and/or a proximal end of the handle. The gripping portion may be configured as any suitable shape that may aid a user's ability to grip the surgical tool assembly such as finger slots, depressions, grooves or a textured surface.

Referring to FIGS. 2A-11D, the striking assembly 10 is configured for releasable attachment to the handle 12. The striking assembly includes a frame 14, an impact plate 18 extending from the frame, and a guard 24 attached to the frame. The striking assembly further includes a locking mechanism 26 for securing the guard in a fixed position relative to the frame. The striking assembly also includes an attachment mechanism 70 for attaching to a surgical tool (not shown) or handle of a surgical tool. In use, the striking assembly facilitates application of an impact force from a striking tool, such as a hammer (not shown). The attachment mechanism allows the striking assembly to releasably attach, e.g., to the handle 12 or to a handle of a surgical tool. The handle 12 may hold and manipulate the surgical tool. A user (e.g., a surgeon) may use the striking assembly in conjunction with the surgical tool to operate on a patient's joint or other body parts. An exemplary surgical tool includes, but is not limited to, an osteotome to remove or extract an implant from bone.

Figure 5:
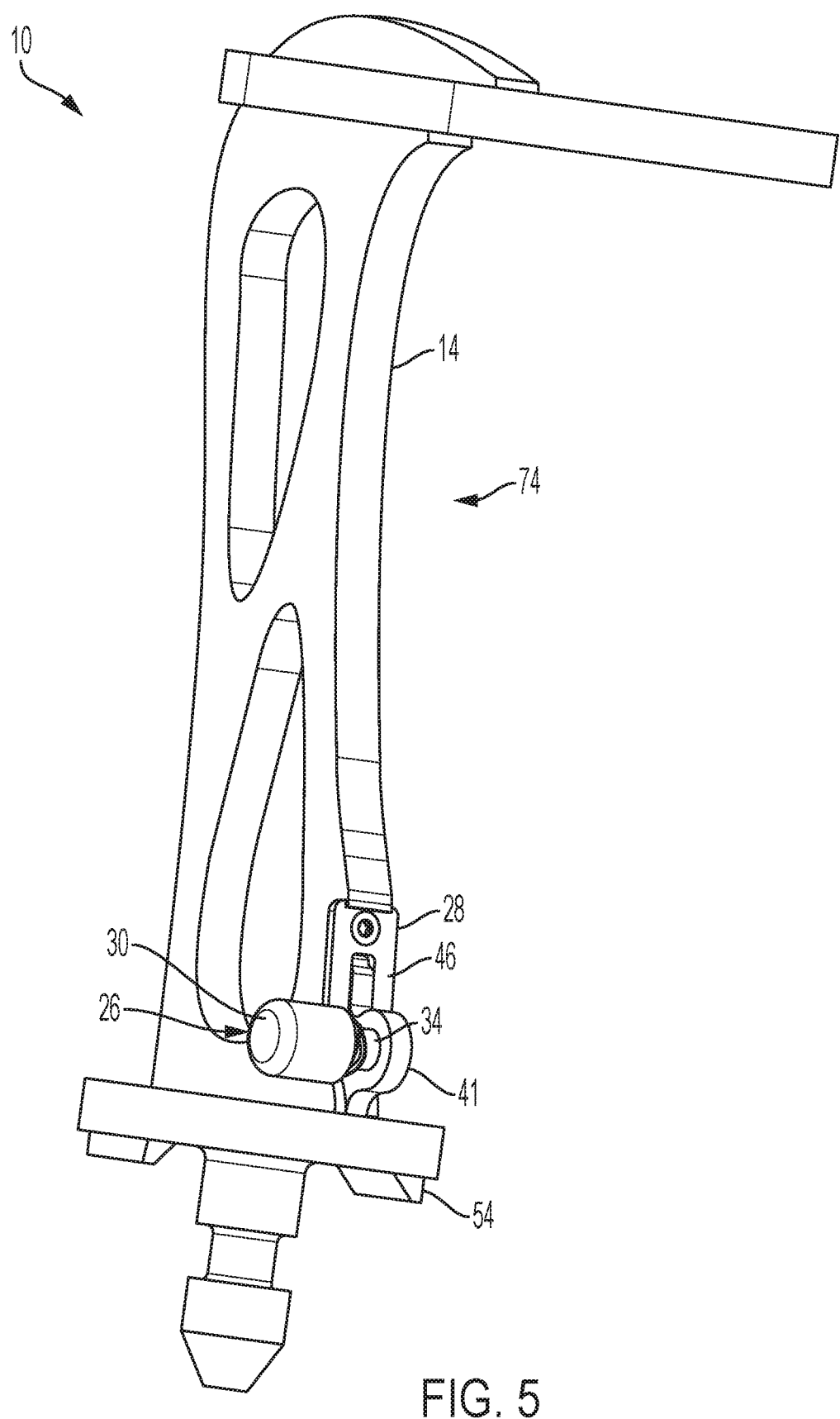
FIG. 5 is a perspective view of the striking assembly of FIG. 2A shown with the guard omitted for purposes of illustration.

The frame 14 includes a main body 74, configured as best shown in FIG. 5, in accordance with an exemplary embodiment. The main body includes a curved anterior side that is shaped to allow a substantially complementarily curved guard 24 to be seated or nested adjacently thereto when in a retracted position. In the exemplary embodiment, the frame 14 is a substantially planar frame having a curved top or proximal end. About the proximal end of the frame is an elongated slot for receiving the implant plate 18 therein. Alternatively, the frame can be a non-planar frame or without a curved anterior face or without a slot, e.g., a cylindrical frame and a planar top for attachment with the impact plate via a fastener, or any other alternative configuration suitable for the intended purpose.

The frame extends a distance between the attachment mechanism 70 and the impact plate 18 to allow sufficient clearance for the striking tool to move or swing so as to provide a force upwardly or downwardly on the impact plate. The impact force can be applied to drive the handle 12 and the tool e.g., into or out of bone or bone cement. The frame allows for a hand of a surgeon on the handle of the surgical tool to be spaced from the impact plate (FIG. 1B) to avoid interference with any striking tools used during a surgical or medical procedure. In accordance with an aspect of the subject disclosure, the frame extends substantially parallel to a longitudinal extent or axis of the handle of the surgical tool when attached thereto. Accordingly, as seen in FIG. 1B, a longitudinal extent or axis of the frame (e.g., Axis A) is substantially aligned with a longitudinal extent or axis of the handle (e.g., Axis B).

Figure 6:
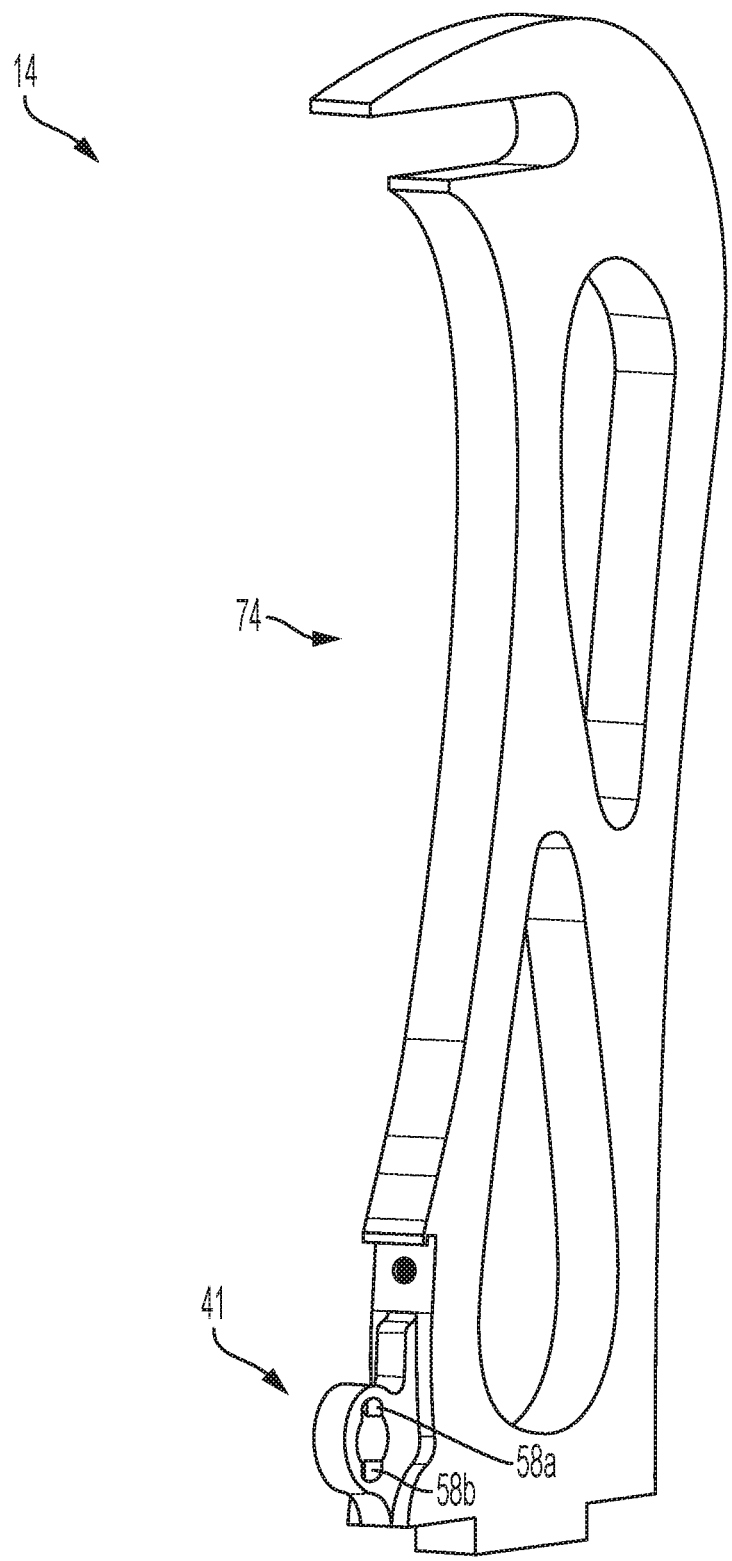
FIG. 6 is a perspective view of a frame of the striking assembly of FIG. 2A.
Figure 7:
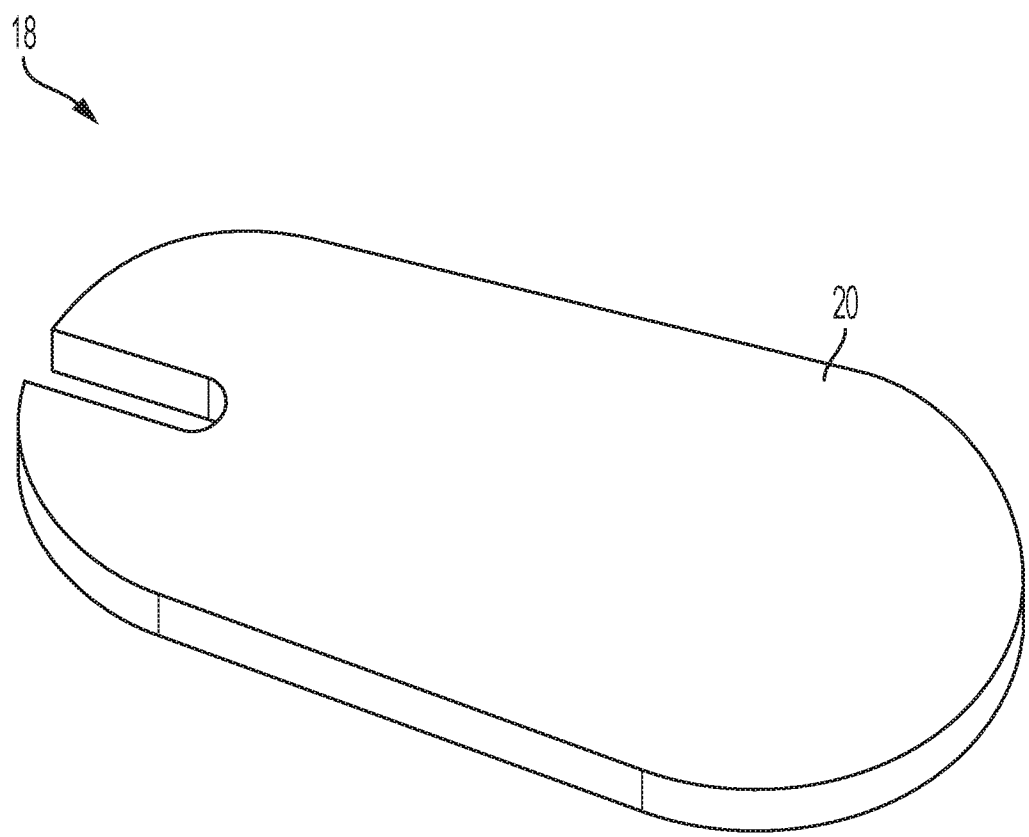
FIG. 7 is a perspective view of an impact plate of the striking assembly of FIG. 2A.

Referring to FIG. 6, the frame 14 includes a positioning member 41 having a first positioning slot 58a and a second positioning slot 58b. By way of non-limiting example, the positioning member may be a fixed truss that is attached to the frame about its distal end. The guard 24 is secured to the frame via the positioning member, as further discussed below. The first and second positioning slots are used to fix or secure the guard in a fixed position, such as a retracted or extended position, respectively.

Figure 2A:
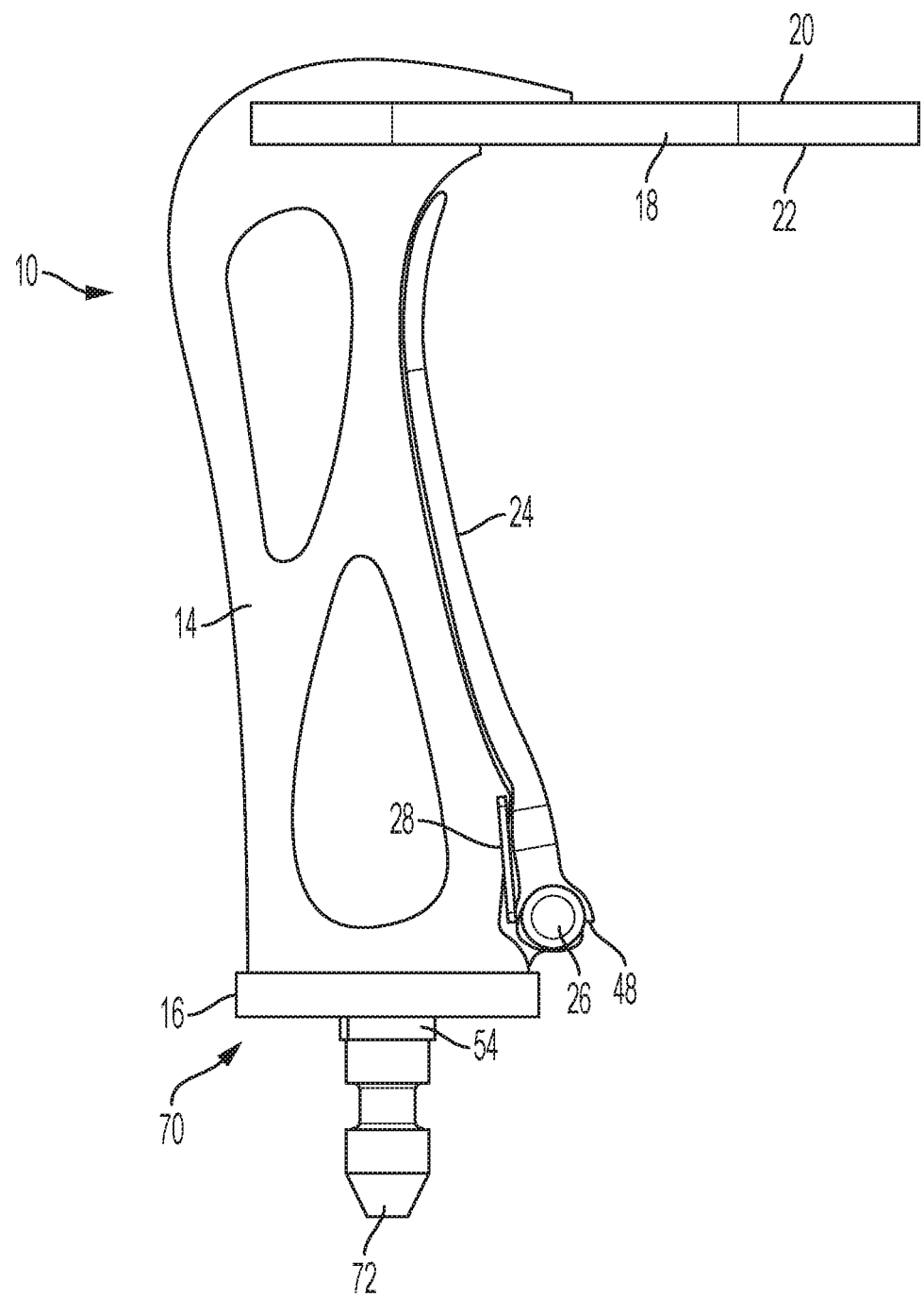
FIGS. 2A-2B are a right side and front view of a striking assembly in accordance with an exemplary embodiment of the subject disclosure with the guard in a retracted position.
Figure 2B:
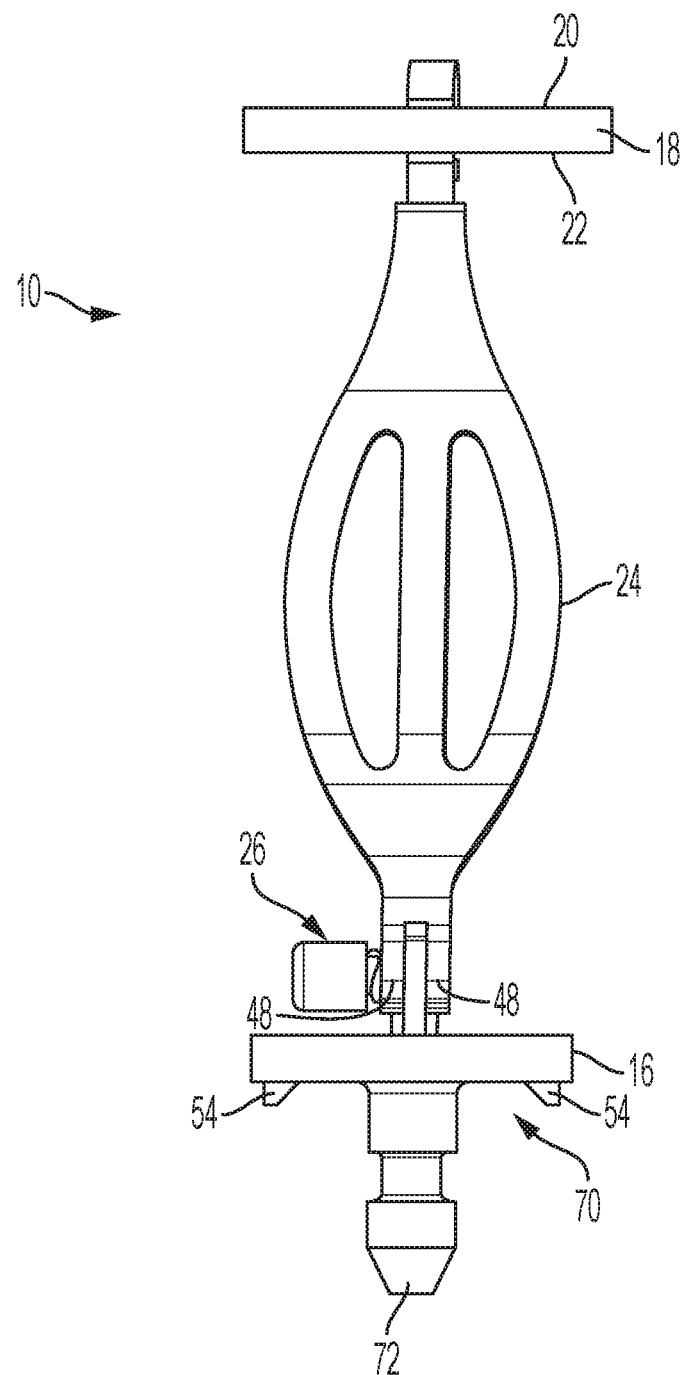
Figure 2C:
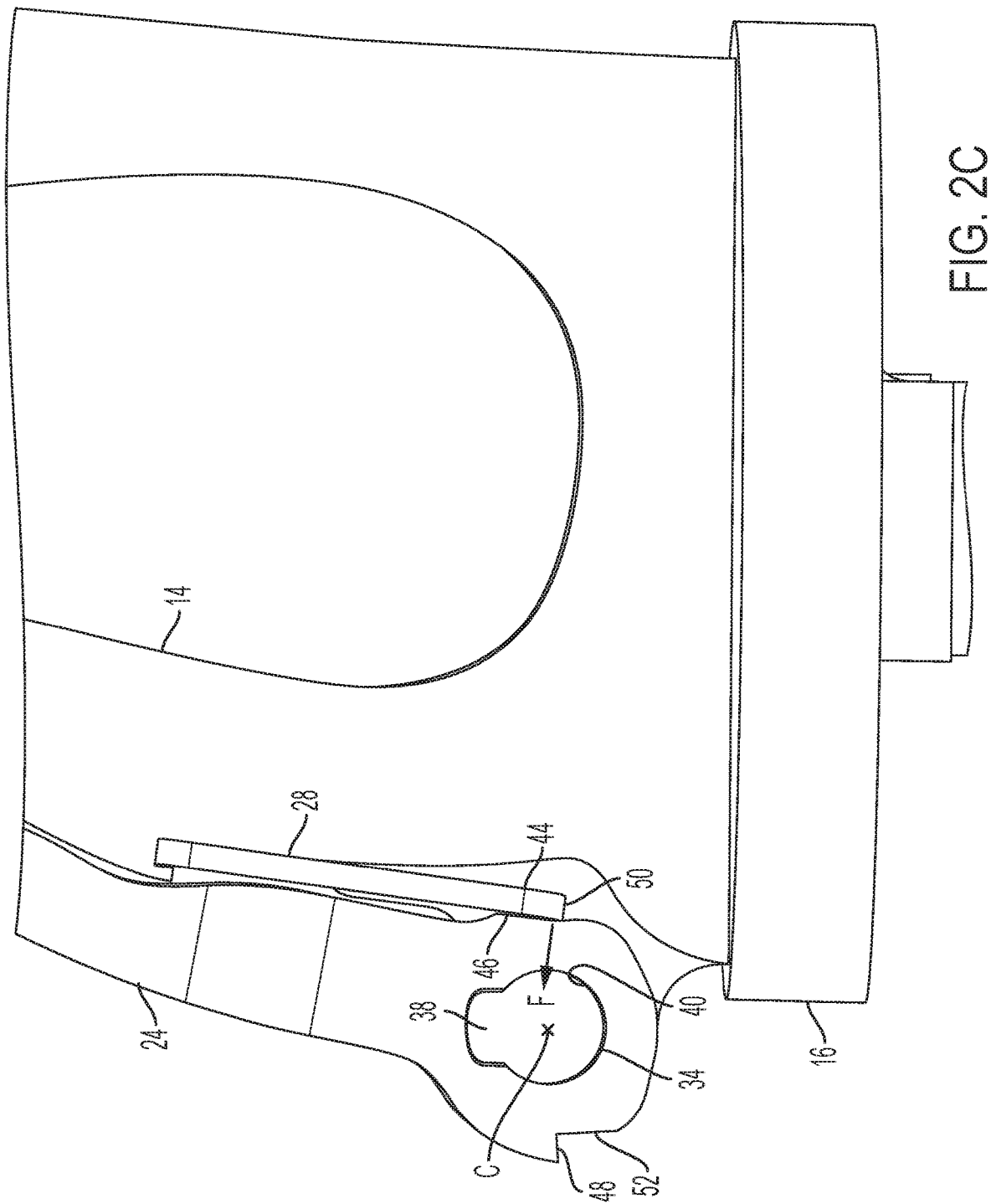
FIG. 2C is an enlarged, partial, left side view of the striking assembly of FIG. 2A shown with the guard in the retracted position.
Figure 3A:
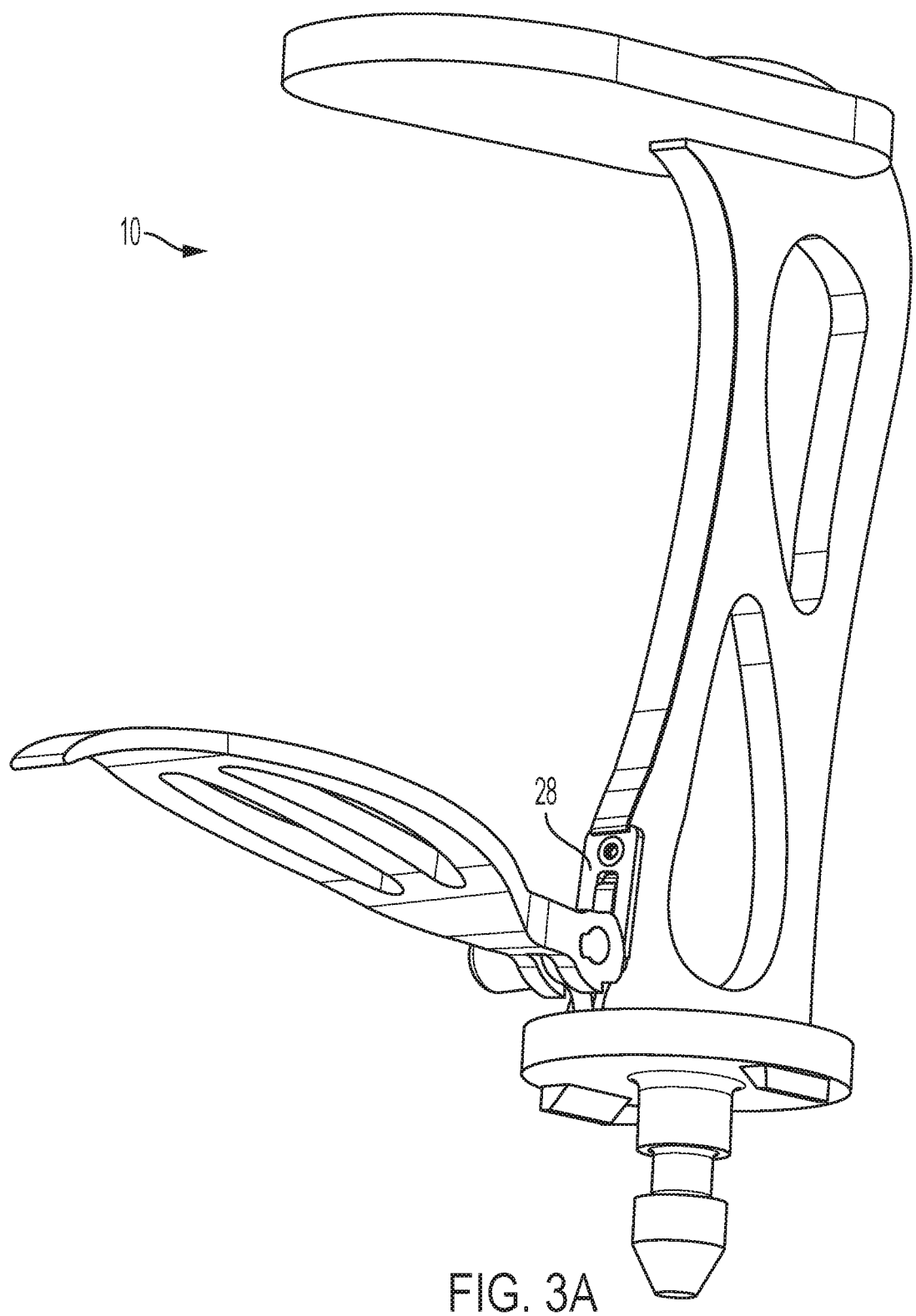
FIG. 3A is a perspective view of the striking assembly of FIG. 2A shown with the guard transitioning between the retracted and extended position.
Figure 3B:
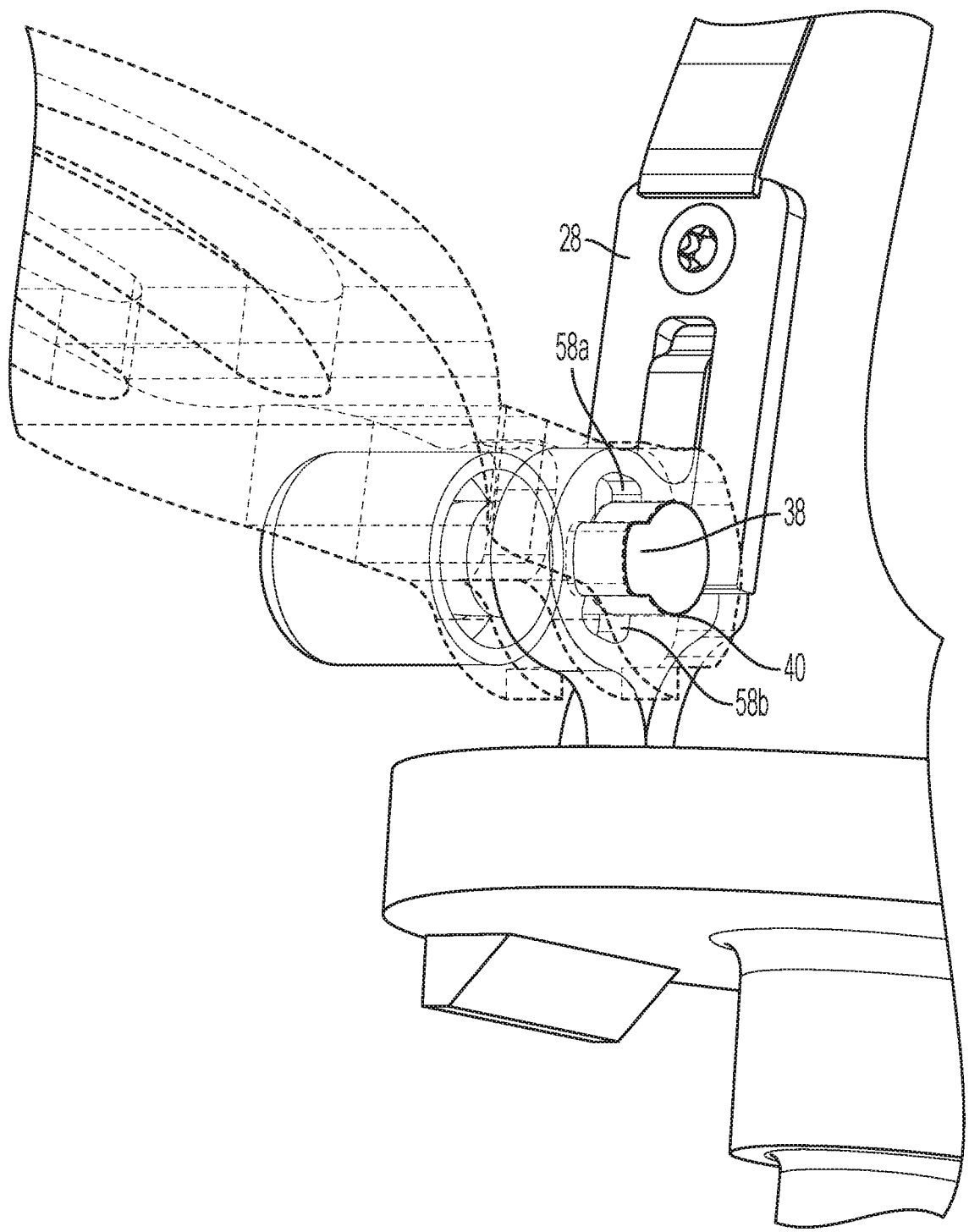
FIG. 3B is an enlarged partial perspective view of the striking assembly of FIG. 2A shown transitioning between the retracted and extended position and with the guard in phantom for purposes of illustration.
Figure 4A:
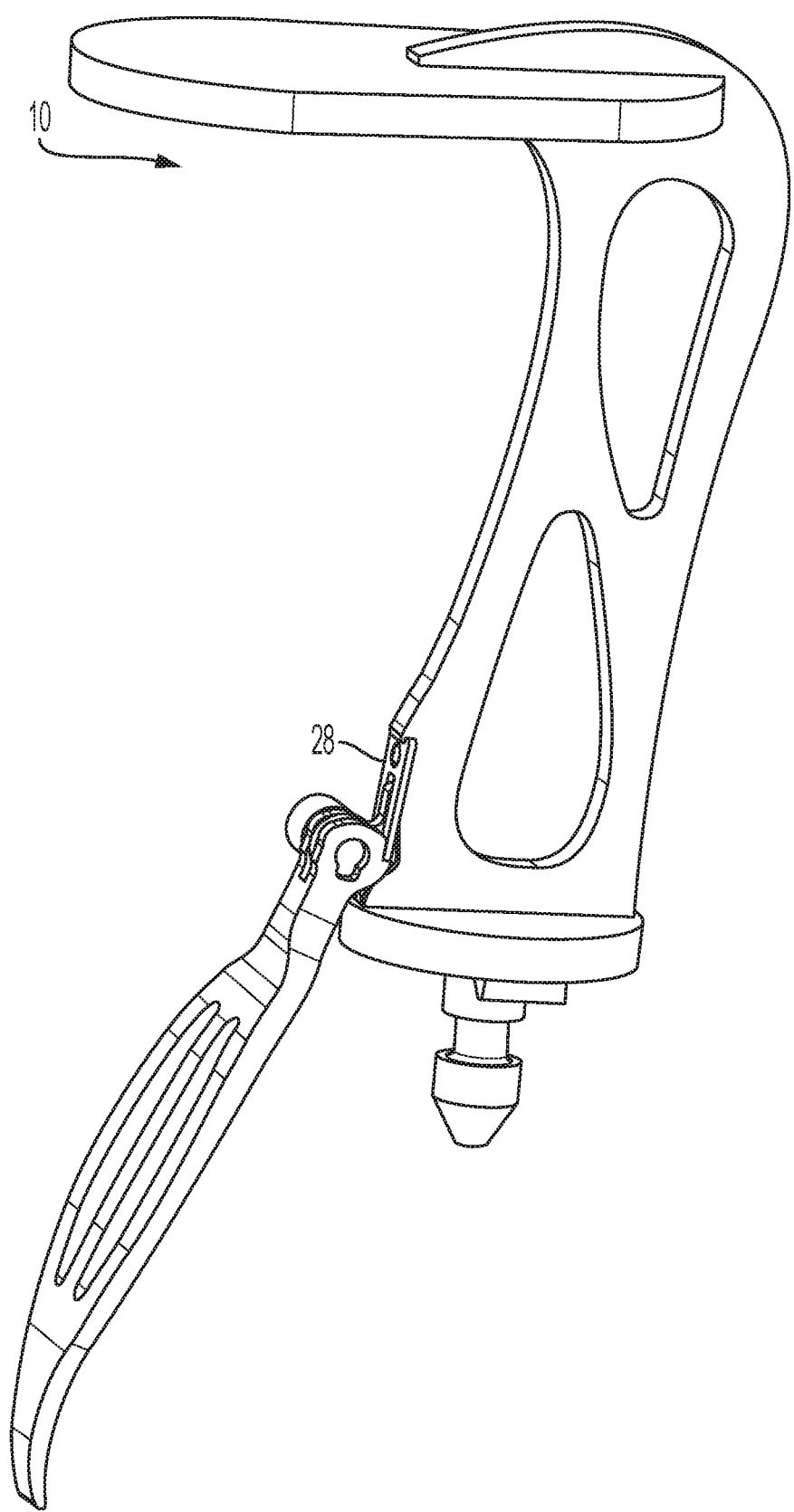
FIG. 4A is a perspective view of the striking assembly of FIG. 2A shown with the guard in the extended position.
Figure 4B:
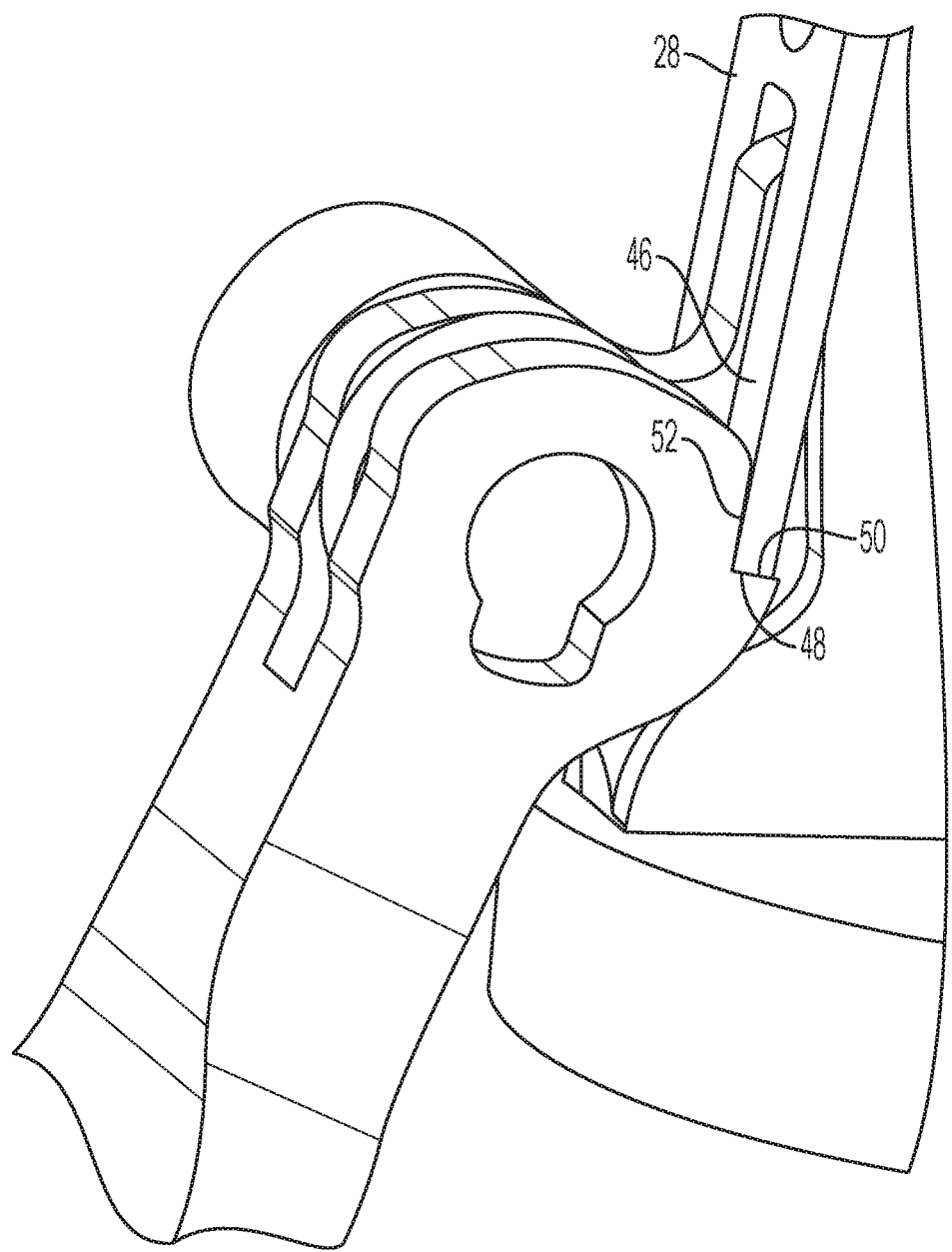
FIG. 4B is an enlarged partial perspective view of the striking assembly of FIG. 2A shown with the guard in the extended position.

Referring to FIGS. 1B, 2A, 2C, 3A, 3B, 4A, 4B, and 5, the frame 14 further includes a biasing actuator 28 fastened to the frame that maintains the guard 24 in a fixed position. In the present embodiment, the biasing actuator is attached to an anterior side of the frame. The biasing actuator is also sometimes referred to herein as a stop. By way of non-limiting example, the biasing actuator may be a spring, and preferably a flat plate-type spring such as a wishbone or leaf spring. Referring to FIG. 5, the biasing actuator has an upper end fastened to the frame 14 and a lower end that projects outwardly from the frame. The biasing actuator operates to bias and maintain the guard in a fixed position, thereby allowing the guard to move and the locking mechanism 26 to matingly engage with the guard. The fixed position of the guard may be a first position, such as a retracted position (FIG. 2A). The fixed position may also be a second position, such as an extended position (FIG. 4A). The biasing actuator operatively engages the guard in the second position (FIG. 4B).

The biasing actuator 28 works with the geometry of the proximal end of the guard to releasably secure the guard 24 in a fixed position (e.g., the retracted or extended position). As best shown in FIG. 2C, the biasing actuator applies a line of force (e.g., Force F) to the guard at a position spaced from a rotational axis (e.g., Axis C) of a locking pin 34 about which the guard pivots to provide a biasing force or torque on the guard. While the guard is in the retracted position, the biasing actuator imparts the biasing force against the proximal end of the guard that torques or biases the proximal end of the guard outwardly (FIGS. 2A-2C), however, the guard is maintained in the retracted position (FIG. 2C) owing to the locking mechanism 26 locking the guard in the retracted position. The substantially mating configuration of the guard body curvature with the curved anterior side of the frame allows the guard to be held closely adjacent the frame in the retracted position. Once the locking mechanism is moved to the unlocking position, the biasing force from the biasing actuator actuates the guard to move the guard to the extended position.

Referring to FIGS. 1A, 2A, and 5, the impact plate 18 of the striking assembly 10 extends from the frame 14. Specifically, the impact plate extends radially outwardly from the frame. The impact plate extends from about a proximal end of the frame (e.g., a top or upper end of the frame) in the anterior direction. As seen in FIG. 1B, the impact plate extends radially outwardly from a longitudinal axis or extent of the frame (e.g., Axis A). The impact plate is adapted to receive an impact force from an unillustrated striking tool, such as a hammer or the like. The striking tool can provide the impact force upwardly or downwardly on the impact plate. For example, the impact can be applied to an upper surface 20 of the impact plate to drive an osteotome or other tool into bone or other bodily tissue. Alternatively, impact forces can be applied to a lower surface 22 of the impact plate to extract the tool from bodily tissue or bone.

Figure 8A:
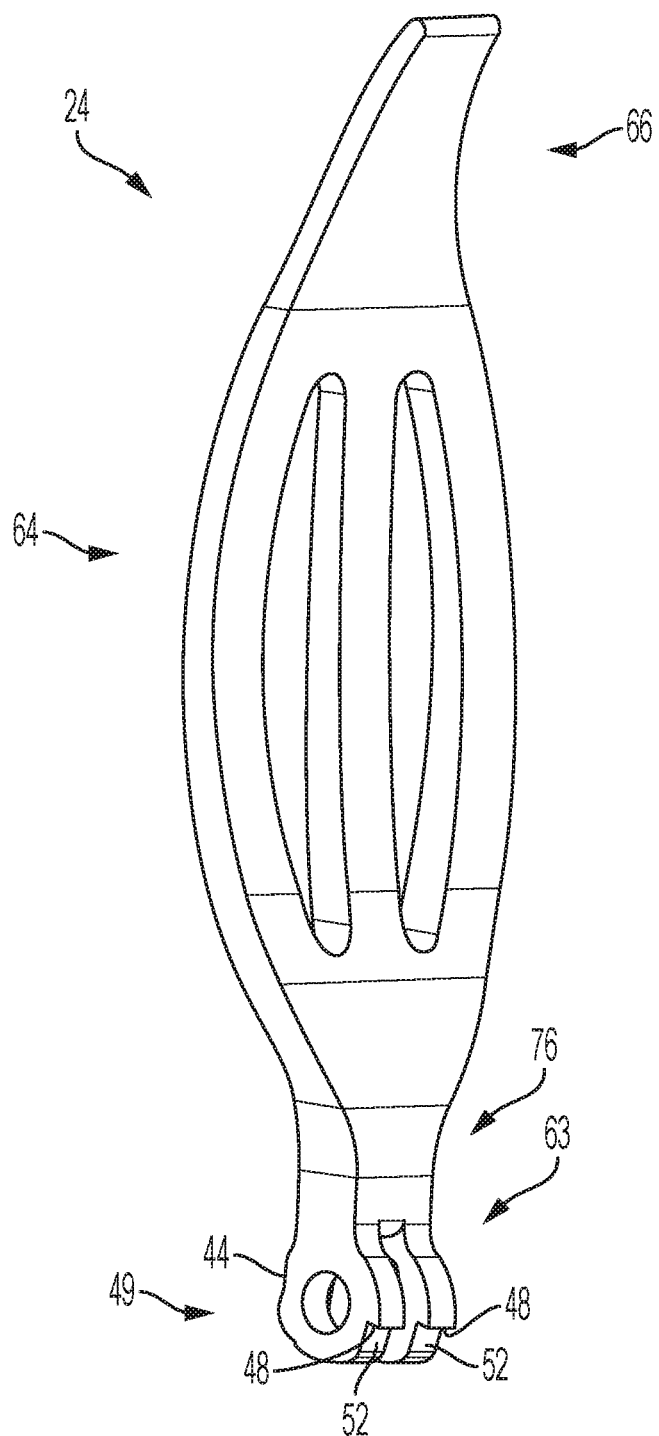
FIGS. 8A-8B are perspective views of a guard of the striking assembly of FIG. 2A.
Figure 8B:
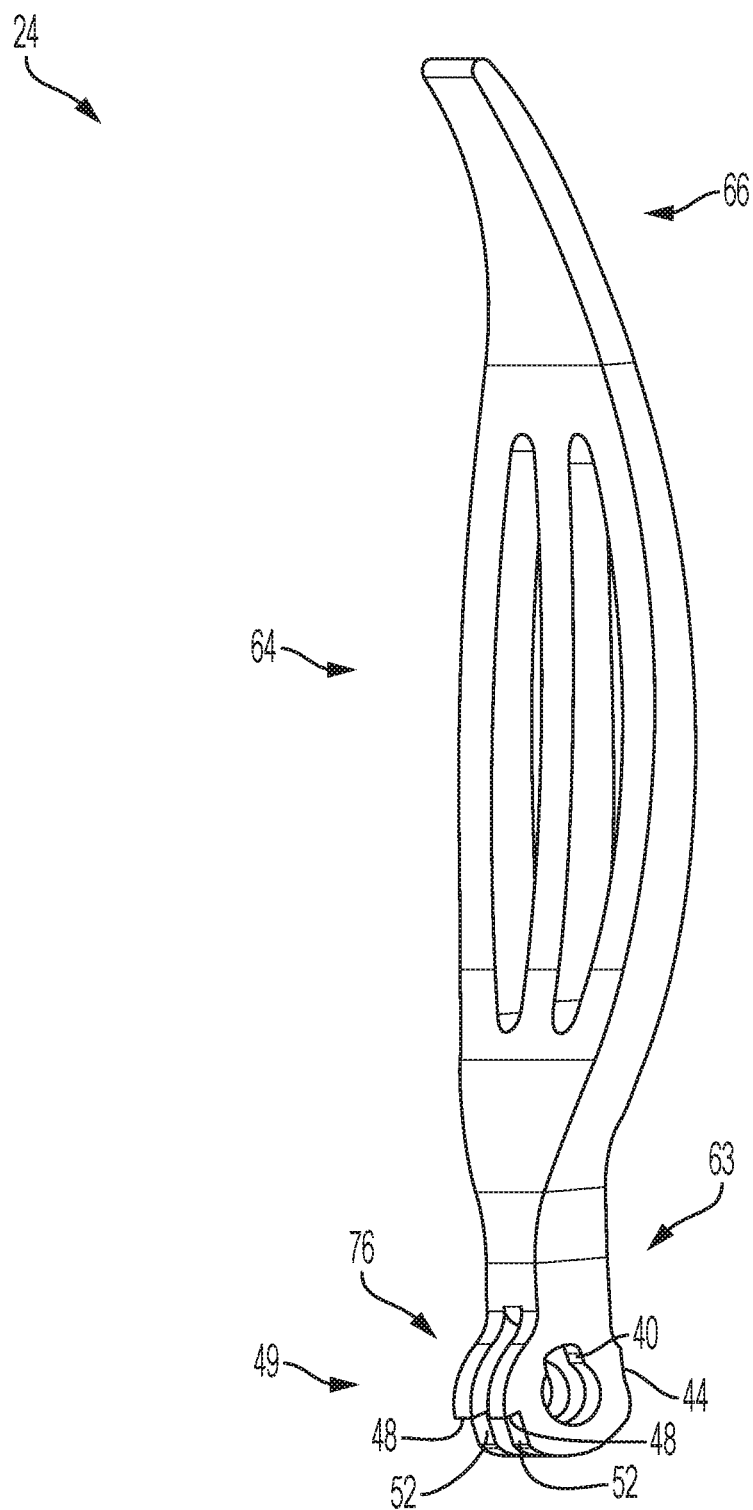

Referring to FIGS. 8A and 8B, the guard 24 of the striking assembly 10 includes a base 63 for attaching to the frame 14, and a curved guard body 64 extending from the base. The guard further includes a curved distal end 66. The base 63 comprises a pivot bracket 76. The guard is attached to an anterior side of the frame via the positioning member 41, about a distal end of the frame. The guard is attached to the same side of the frame that the impact plate 18 extends from (FIGS. 2A, 4A).

The guard 24 is attached to the frame 14 and movable between a plurality of positions. For example, the guard is positionable into a fixed position, and is movable between the first position adjacent the frame (FIG. 1A) and the second position distal to the frame (FIG. 1B). The first position is also referred to herein as a retracted position and the second position is also referred to herein as an extended position.

The guard 24 is releasably securable into each of the retracted and extended positions. In other words, the retracted position may correspond to a first position adjacent the frame 14 (FIG. 1A) and the extended position may correspond to a second position adjacent the handle 12 (FIG. 1B). For example, in the extended position, the guard protects the knuckles of a user's hand while the user grasps the handle and strikes either downwardly or upwardly on the impact plate 18 with a striking tool such as a hammer. In the second position the guard is laterally adjacent the handle. Specifically, in the second position the guard is laterally adjacent a majority of a longitudinal length of the handle (FIG. 1B). In the second position, the curved guard body 64 is distally spaced from a distal end of the frame 14.

Referring to FIG. 2C, the pivot bracket 76 includes a rear surface 44 and a stop 48. The pivot bracket includes a posterior end having a flat geometry for engaging the biasing actuator 28 in the retracted position. For example, the flat geometry can be flat surfaces defining the rear surface of the pivot bracket (FIGS. 2C, 8A, 8B). In the retracted position, the flat surface of the guard is operable to matingly conform to a flat front face 46 of the biasing actuator 28 of the frame 14. In the first position, the guard body is laterally adjacent the frame. Specifically, in the first position the guard body is laterally adjacent a majority of a longitudinal length of the frame. As seen in FIG. 2C, while the guard is in the retracted position, the biasing actuator imparts a biasing force against the proximal end 49 of the guard that biases the proximal end of the guard to torque about the rotational axis (e.g., Axis C), however the guard is maintained in the retracted position owing to the locking mechanism 26 locking the guard in the retracted position. The substantially mating configuration of the guard body curvature with the curved anterior side of the frame allows the guard to be closely held adjacent the frame in the retracted position, e.g., in a nested or seated position.

Referring to FIGS. 4B, 8A, and 8B, the pivot bracket 76 of the guard 24 further includes a shoulder or pair of shoulders or pair of stops 48 and a second flat surface 52 about its anterior side. To help secure the guard in the second position, the stops provided on the distal end of the guard come into abutment with the distal end 50 of the biasing actuator 28 (FIG. 4B). The rotation of the guard is stopped upon engagement of the stops by the distal end of the biasing actuator. In this position the locking slot 40 of the pivot bracket is aligned with the key 38 of the locking pin 34 to secure the guard in the extended position.

Figure 11A:
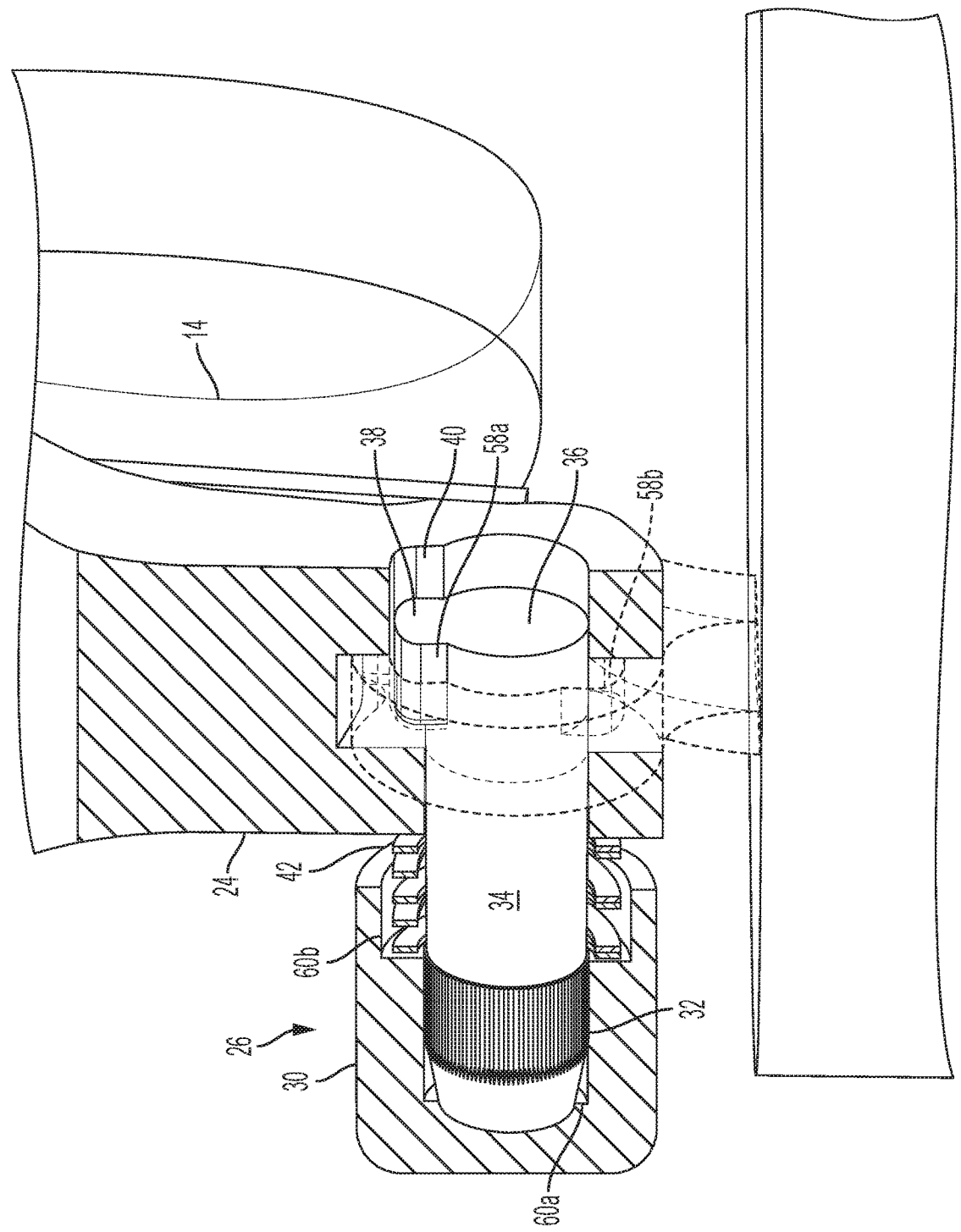
FIG. 11A is an enlarged partial front perspective view of a locking mechanism of the striking assembly of FIG. 2A with various components shown in a front cross-sectional view and with the frame shown in phantom for purposes of illustration.

Referring to FIGS. 1A-2C, 4A, and 11A, the locking mechanism 26 of the striking assembly 10 locks or secures the guard 24 in a fixed position relative to the frame. The fixed position may be an extended or a retracted position. The locking mechanism is also referred to herein as a lock. Referring to FIG. 11A, the locking mechanism includes a keyed locking pin 34 movable relative to the positioning member 41 between an unlocking position and a locking position. The locking mechanism further includes a button 30 and a biasing member 42. The locking mechanism releasably secures the guard in the retracted or extended position. Generally, the retracted position is a non-hand-guarding position and the extended position is a hand-guarding position. The locking mechanism provides a quick release mechanism that allows the user to rotate the guard quickly and efficiently between the retracted position and the extended position upon pushing the button 30 toward the frame 14 which thereby allows the guard to rotate automatically into the desired fixed position.

Figure 9:
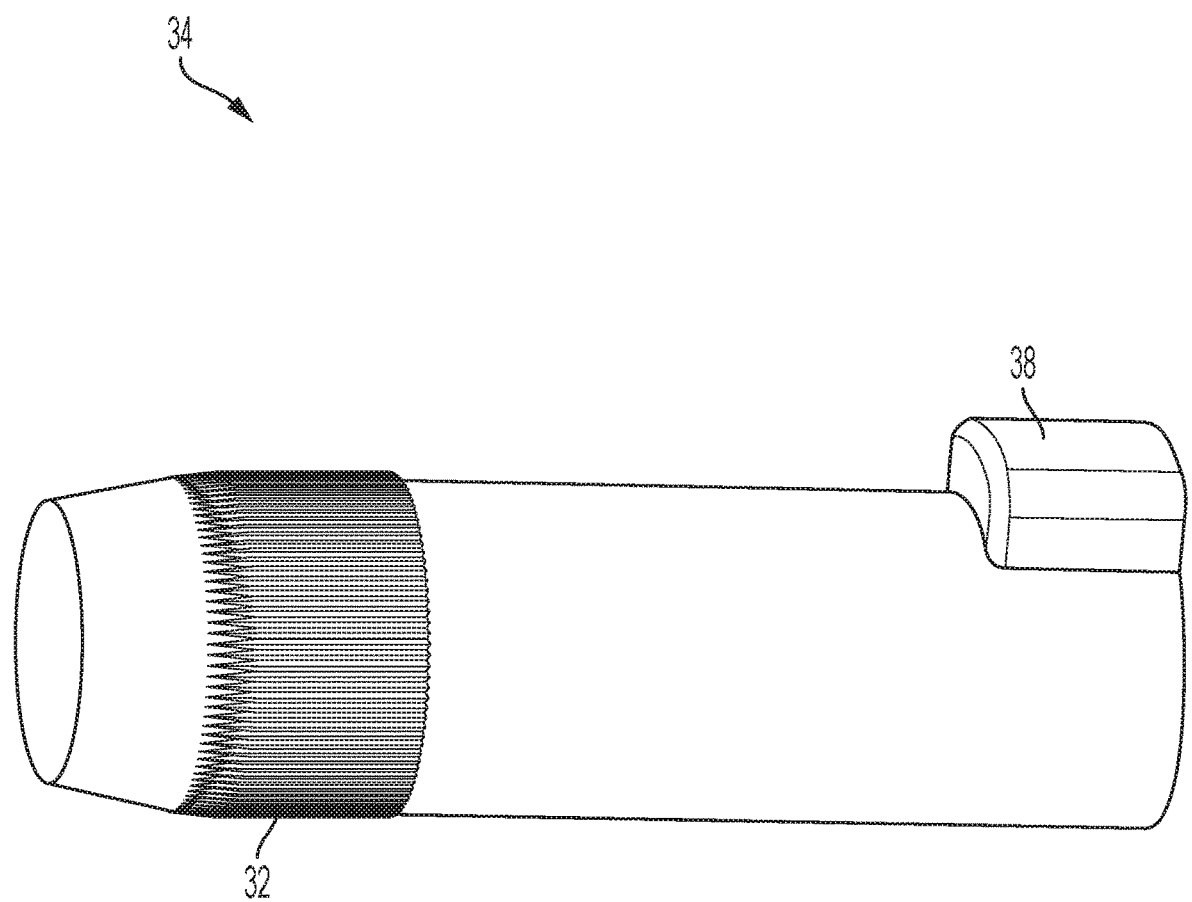
FIG. 9 is a perspective view of a locking pin of the striking assembly of FIG. 2A.

Referring to FIGS. 9 and 11A, the keyed locking pin 34 includes a distal end having a plurality of grooves 32 circumscribing the pin. The grooves may be knurled using a pattern that facilitates attachment of the button 30 with the locking pin. As illustrated in the exemplary embodiment, the grooves may be formed in a straight-line pattern, although angled patterns, crossed lines, diamond patterns, or any other pattern may be used that facilitates a gripping connection between the locking pin and the button. The distal end also includes a chamfer for aiding in inserting the locking pin in the button. About its proximal end, the locking pin includes a key 38 that protrudes radially outwardly. The key is shaped to matingly engage with the locking slot 40 on the pivot bracket 76 of the guard 24. The key is also shaped to matingly engage with the first positioning slot 58a and the second positioning slot 58b of the positioning member 41 of the frame 14. In operation, when the user pushes the button inwardly towards the frame, the locking mechanism is moved into the unlocking position, e.g., the key is moved into the locking slot of the pivot bracket. In other words, the longitudinal force from the button operates to slide the key proximally into mating engagement with the locking slot on the guard. As seen in FIGS. 3A, 3B, and 11C, once the button is depressed toward the frame, the key is slid out of the first positioning slot or the second positioning slot and matingly engaged with the locking slot on the guard such that the guard becomes rotatable about the locking pin.

Figure 10:
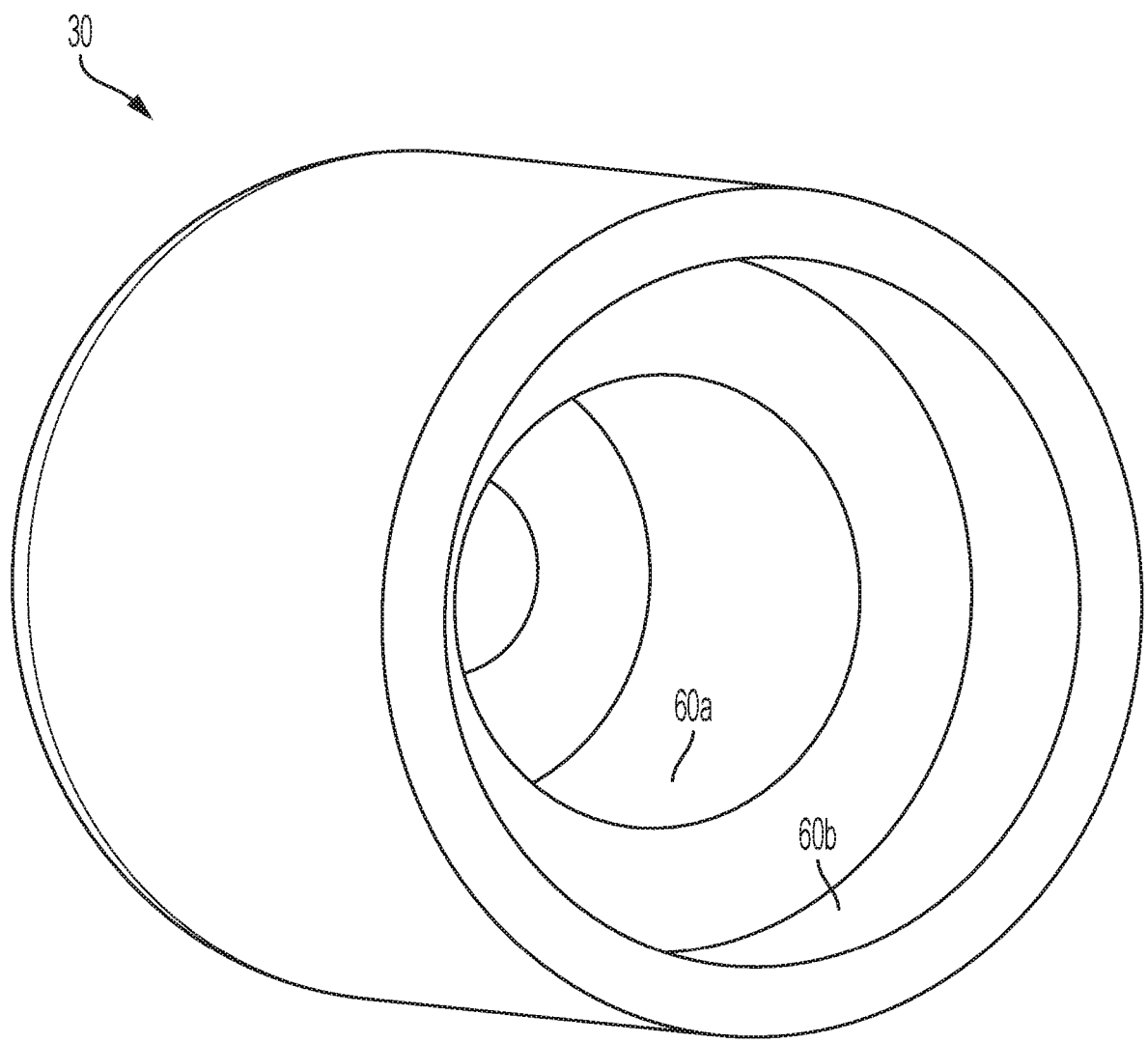
FIG. 10 is a perspective view of a button of the striking assembly of FIG. 2A.

Referring to FIGS. 10 and 11A, the button 30 includes a recess 60a for receiving the keyed locking pin 34 and another recess 60b for receiving the biasing member 42. When a user (e.g., a surgeon) desires to move the guard 24 from the retracted to the extended position, the user pushes the button inwardly towards the frame 14. The locking mechanism 26 allows the guard 24 to be rotated downwardly into the extended position shown in FIGS. 1B, 4A, and 4B owing to the biasing force provided by the biasing actuator 28, or upwardly into the retracted position as shown in FIGS. 1A and 2A-2C.

The biasing member 42 biases the locking mechanism 26 towards its locking position for mating with the positioning member 41 of the frame 14. The biasing member may be a spring or similar biasing member. When the button 30 is released while the guard 24 is in either the retracted or extended positions, the biasing member imparts a force outwardly on the button to bias the key 38 of the locking pin 34 in a respective positioning slot on the positioning member.

Referring to FIGS. 1A, 1B, 2A, and 2B, the striking assembly 10 further includes an attachment mechanism 70 for attaching to a surgical tool. The attachment mechanism includes a quick connect 72 and a pair of detents 54. The attachment mechanism further includes a base 16. The attachment mechanism allows for releasably securing the striking assembly 10 to the surgical tool handle 12 via the base 16.

The quick connect 72 extends downwardly from the base 16 for facilitating a fast and efficient connection with, e.g., a handle of a surgical tool. The quick connect operatively engages a cooperating quick connect female end, for example on a locking assembly 55 of the handle 12.

The detents 54 extend downwardly from the base 16 for locking the base in a fixed position relative to the surgical tool handle. The detents 54 operatively engage cooperating detents on the handle 12. Specifically, the detents are configured for selectively engaging a plurality of chamfered edges 53 circumferentially positioned about a periphery of the locking assembly 55 of the handle. Accordingly, the striking assembly 10 can be releasably secured in a fixed position about a plurality of rotational positions relative to the longitudinal axis of the surgical tool handle by a locking mechanism. Exemplary locking mechanisms applicable to the present disclosure include, e.g., the locking mechanisms described in International Patent Application Number PCT/US17/49492 entitled "OSTEOTOME," the entire contents of which are incorporated by reference herein for all purposes.

Figure 11B:
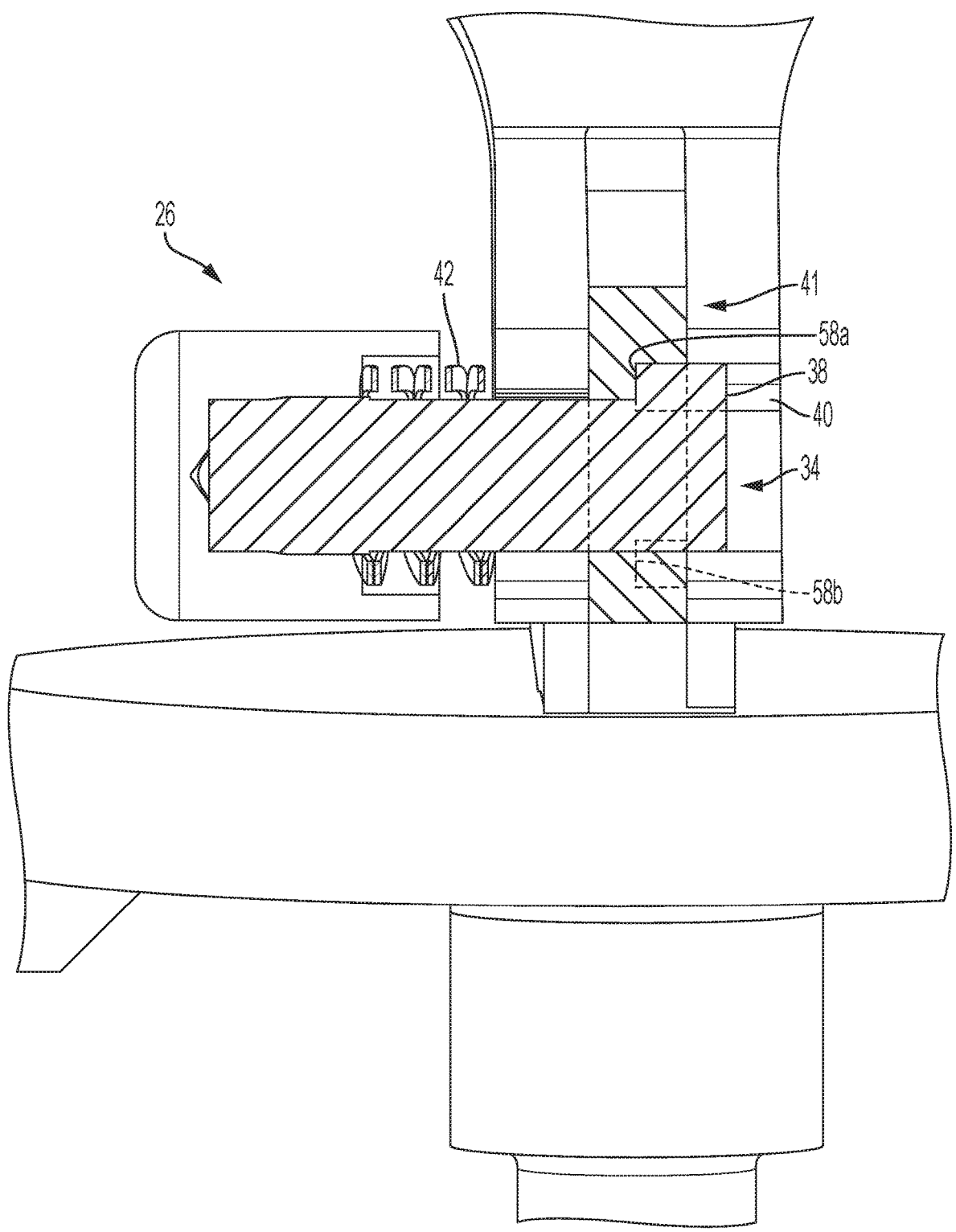
FIGS. 11B-11D are enlarged partial front cross-sectional views of the locking mechanism of the striking assembly of FIG. 2A in a locking and an unlocking position taken along a frontal plane.
Figure 11C:
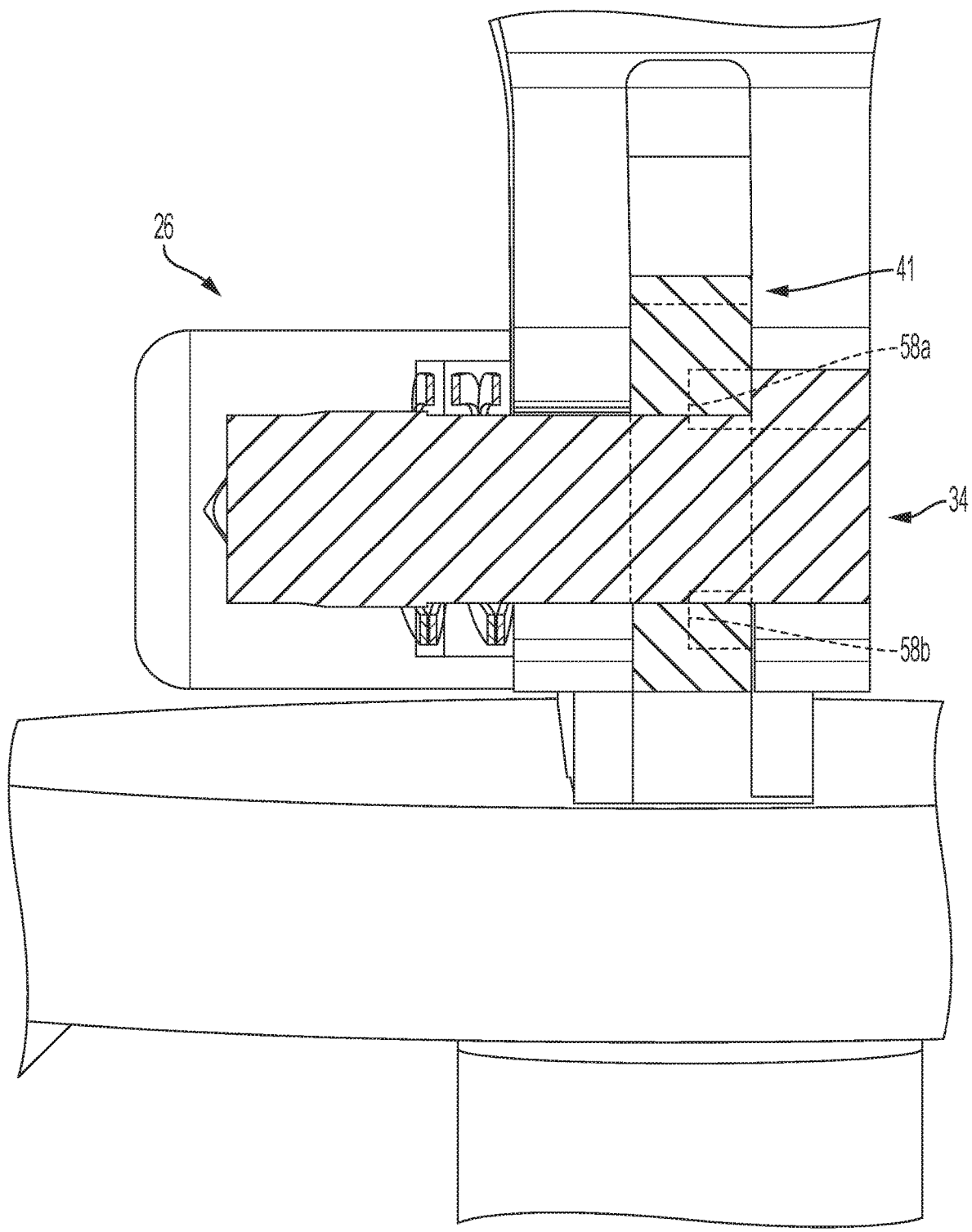

In operation, FIGS. 2C, 11A, and 11B illustrate the locking mechanism 26 in its locking position with the guard 24 in the retracted position. In this configuration, the biasing member 42 of the locking mechanism 26 operates to seat the key 38 of the locking pin 34 partially into the first positioning slot 58a of the frame 14 while the key remains partially seated in the locking slot 40 of the pivot bracket 76 of the guard (FIGS. 11A, 11B). Specifically, the biasing member operates to bias the button 30 and the locking pin 34 outwardly away from the frame. When the locking mechanism 26 is in its locking position, the key 38 is partially seated in the first positioning slot of the frame and partially seated in the locking slot of the guard. This configuration prevents the guard 24 from being able to rotate about the locking pin from the retracted position, thereby securing the guard in the retracted position.

Figure 11D:
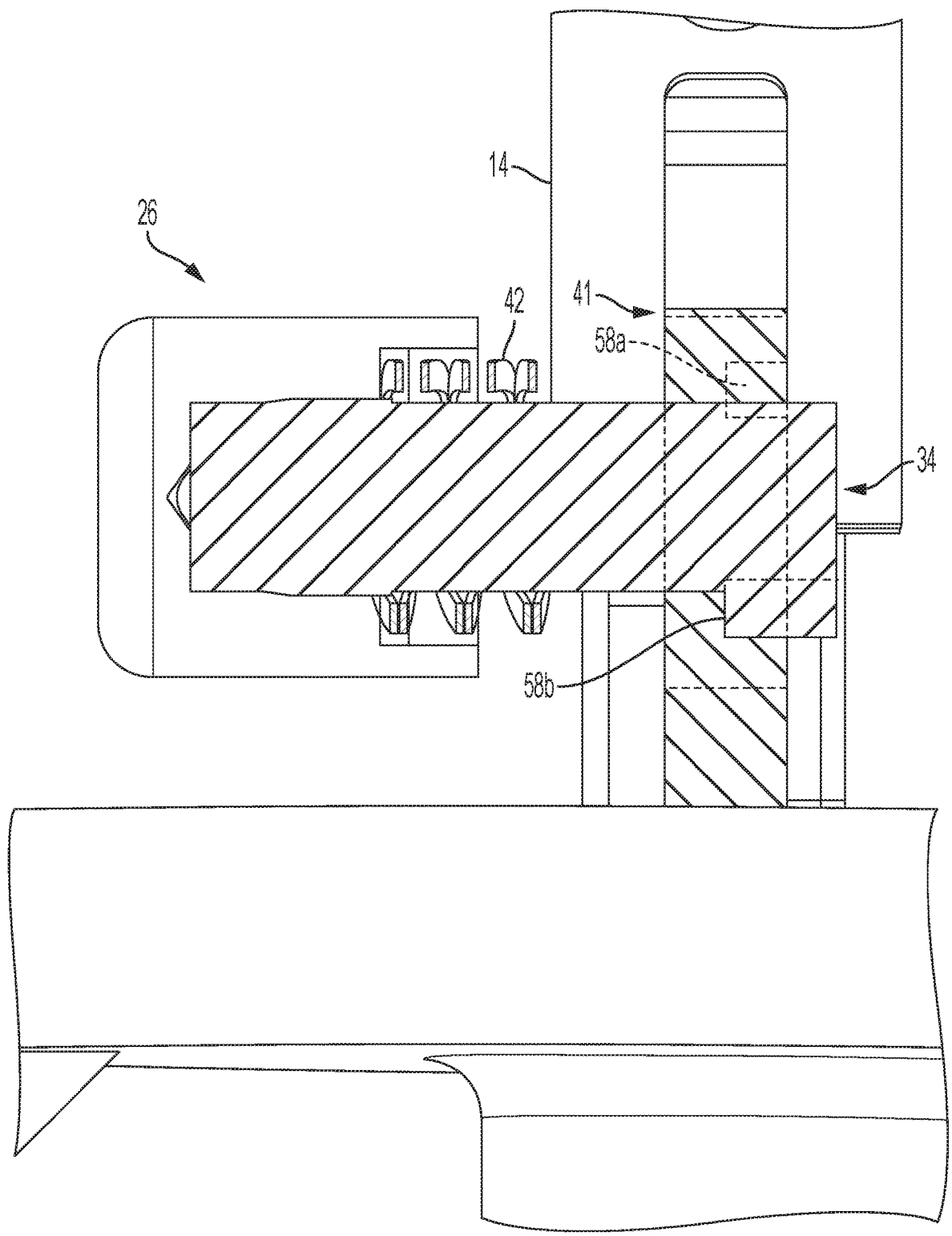

Referring to FIG. 11C, in operation when a user desires to move the guard 24 to the extended position, the user pushes the button 30 inwardly towards the frame 14, thereby moving the locking mechanism 26 into its unlocking position. Pushing the button operates to counter the bias of the biasing member 42 and imparts a longitudinal force proximally on the locking pin 34 that slides the key 38 clear of the first positioning slot 58a of the frame 14 and into fully mating engagement with the locking slot 40 of the guard. When the locking mechanism 26 is in this unlocked configuration with the button depressed, the guard is rotated downwardly about the locking pin 34 (FIGS. 3A, 3B) into the extended position (FIGS. 4A, 4B) owing to the biasing force applied to the pivot bracket 76 by the biasing actuator 28 which imparts a torque onto the guard relative to a rotational axis of the locking pin 34. For example, the biasing actuator operates in conjunction with the button 30 as a quick release mechanism to quickly and efficiently actuate the guard 24 to rotate downwardly about the locking pin 34. When the button is released (i.e., the locking mechanism is in its locking position) and the guard is in the 0extended position, the key 38 is partially seated in the second positioning slot 58b of the frame and partially seated in the locking slot of the guard (FIG. 11D). This configuration prevents the guard 24 from being able to rotate about the locking pin from the extended position back to the retracted position, thereby securing the guard in the extended position.

Referring to FIG. 1B, in the extended position the guard 24 operates to protect a hand of a user (e.g., a surgeon) from harm when the user is holding a surgical tool handle and imparting an impact force on the striking assembly with a striking tool. That is, the guard provides protection to the user's hand on the handle 12. Specifically, the guard protects the hand of the user from being hit by a striking tool such as a hammer when the guard is moved to the extended position covering the user's hand gripping the handle.

In operation when the user desires to return the guard to the retracted position, the user pushes the button 30 inwardly toward the frame 14 and pulls forwardly and upwardly on the guard 24. This motion overcomes the mating contact of the second flat surface 52 with the flat front face 46 of the biasing actuator 28 of the frame (FIG. 4B). The user continues to rotate the guard until the first flat face 44 of the pivot bracket 76 returns to face-to-face contact with the flat front face of the biasing member (FIG. 2C). Once the guard is in the retracted position, releasing the button returns the key 38 partially into the first positioning slot 58a of the frame 14 (FIGS. 11A, 11B), which receives the guard in the retracted position. While the biasing actuator exerts a biasing force on the pivot bracket outwardly from the frame 14, the locking mechanism 26 operates to maintain the guard in the retracted position.

The exemplary embodiments described herein provide numerous advantages over conventional striking assemblies for surgical tools. For example, one advantage of the exemplary striking assembly embodiment is use of a lock, e.g., locking mechanism 26 in combination with frame 14 and guard 24, which when in the locking position secures the guard in the positioning member of the frame and serves to secure the guard in a fixed position (e.g., the retracted or extended position) and prevents the guard from being rotatable to an undesired position.

Another advantage of the exemplary striking assembly embodiment is use of a quick release mechanism, e.g., biasing actuator 28 and locking mechanism 26, which provides for quick and efficient transitions of the guard 24 from the retracted to the extended position. For example, the present striking assembly uses the button 30 of the locking mechanism in combination with the biasing actuator to provide one-handed operation to move the guard to the extended position by pushing the button inwardly towards the frame.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

I claim:

1. A striking assembly for attachment to a surgical tool, comprising:
a frame;
an impact plate extending from about a proximal end of the frame; and
a guard attached to about a distal end of the frame and movable between a first position adjacent the frame and a second position distal to the frame,
wherein, in the second position, the guard is configured to protect a user's fingers from being struck by a striking tool used to strike the impact plate.

2. The striking assembly of claim 1, further comprising a lock mechanism for securing the guard in a fixed position relative to the frame.

3. The striking assembly of claim 1, further comprising an attachment mechanism for attaching to a surgical tool.

4. The striking assembly of claim 1, wherein the impact plate extends radially outwardly from the frame.

5. The striking assembly of claim 1, wherein the guard is attached to the same side of the frame that the impact plate extends from, or wherein the guard is attached to an anterior side of the frame.

6. The striking assembly of claim 1, wherein the frame includes a positioning member having a first and a second positioning slot, and the guard is secured to the frame via the positioning member.

7. The striking assembly of claim 6, further comprising a lock that includes a keyed locking pin movable relative to the positioning member between an unlocking position and a locking position wherein in the locking position the keyed locking pin engages one of the first or second positioning slots.

8. The striking assembly of claim 7, wherein the lock further comprises a biasing member biasing the keyed locking pin to the locking position.

9. The striking assembly of claim 1, wherein the frame further comprises a stop to operatively engage the guard in the second position.

10. The striking assembly of claim 1, wherein the frame further comprises a biasing actuator to operatively actuate the guard into the second position.

11. The striking assembly of claim 1, the guard comprising:
a base for attaching to the frame; and
a curved guard body extending from the base, wherein when in the second position, the curved guard body is distally spaced from a distal end of the frame.

12. The striking assembly of claim 11, wherein the guard further comprises a curved distal end.

13. A surgical tool assembly comprising:
a handle for attachment to a tool; and
a striking assembly for attachment to the handle, the striking assembly including:
a frame, an impact plate extending from the frame, and a guard attached to the frame and movable between a first position adjacent the frame and a second position adjacent the handle, wherein, in the second position, the guard is laterally adjacent a majority of a longitudinal length of the handle and is configured to protect a user's hand from being struck by a striking tool used to strike the impact plate.

14. The surgical tool assembly of claim 13, wherein in the second position the guard is laterally adjacent the handle.

15. The surgical tool assembly of claim 13, wherein the guard is attached to an anterior side of the frame.

16. The surgical tool assembly of claim 13, wherein the handle attaches to a distal end of the striking assembly and a longitudinal axis of the handle is substantially aligned with a longitudinal axis of the frame of the striking assembly.

17. The surgical tool assembly of claim 13, wherein the striking assembly further comprises an attachment mechanism for attaching to the handle, the attachment mechanism including:

a pair of detents for operatively engaging cooperating detents on the handle.

18. A surgical tool assembly comprising:

a handle for attachment to a tool; and a striking assembly for attachment to the handle, the striking assembly including:

a frame, an impact plate extending from the frame and having a longitudinal axis transverse to a longitudinal axis of the frame, a guard attached to the frame and movable between a first position adjacent the frame and a second position adjacent the handle, and an attachment mechanism for attaching to the handle.

* * * * *